US009968710B2

(12) United States Patent
Duewelhenke

(10) Patent No.: US 9,968,710 B2
(45) Date of Patent: *May 15, 2018

(54) PHARMACEUTICAL COMPOSITION, SUBSTRATE COMPRISING A PHARMACEUTICAL COMPOSITION, AND USE OF A PHARMACEUTICAL COMPOSITION

(71) Applicant: Biomet Deutschland GmbH, Berlin (DE)

(72) Inventor: Nicole Duewelhenke, Berlin (DE)

(73) Assignee: Biomet Deutschland GmbH, Berlin (DE)

( * ) Notice: Subject to any disclaimer, the term of this patent is extended or adjusted under 35 U.S.C. 154(b) by 147 days.

This patent is subject to a terminal disclaimer.

(21) Appl. No.: 14/566,465

(22) Filed: Dec. 10, 2014

(65) Prior Publication Data

US 2015/0157766 A1 Jun. 11, 2015

Related U.S. Application Data

(62) Division of application No. 12/670,354, filed as application No. PCT/EP2008/006046 on Jul. 23, 2008, now Pat. No. 8,921,365.

(30) Foreign Application Priority Data

Jul. 23, 2007 (EP) ..................................... 07075639

(51) Int. Cl.
*A61K 31/4709* (2006.01)
*A61K 31/65* (2006.01)
*A61K 31/7048* (2006.01)
*A61K 31/7088* (2006.01)
*A61K 31/16* (2006.01)
*A61K 31/395* (2006.01)
*A61K 31/496* (2006.01)
*A61L 27/54* (2006.01)
*A61K 31/665* (2006.01)
*A61K 38/12* (2006.01)
*A61K 45/06* (2006.01)
*A61L 31/16* (2006.01)
*A61F 2/32* (2006.01)
*A61F 2/38* (2006.01)
*A61F 2/40* (2006.01)
*A61F 2/44* (2006.01)
*A61K 31/7036* (2006.01)
*A61K 38/08* (2006.01)
*A61L 27/06* (2006.01)
*A61L 27/28* (2006.01)

(52) U.S. Cl.
CPC ................ *A61L 27/54* (2013.01); *A61F 2/32* (2013.01); *A61F 2/38* (2013.01); *A61F 2/3804* (2013.01); *A61F 2/40* (2013.01); *A61F 2/44* (2013.01); *A61K 31/395* (2013.01); *A61K 31/4709* (2013.01); *A61K 31/496* (2013.01); *A61K 31/65* (2013.01); *A61K 31/665* (2013.01); *A61K 31/7036* (2013.01); *A61K 31/7048* (2013.01); *A61K 31/7088* (2013.01); *A61K 38/08* (2013.01); *A61K 38/12* (2013.01); *A61K 45/06* (2013.01); *A61L 27/06* (2013.01); *A61L 27/28* (2013.01); *A61L 31/16* (2013.01); *A61L 2300/406* (2013.01); *A61L 2300/45* (2013.01); *A61L 2420/06* (2013.01)

(58) Field of Classification Search
CPC .. A61K 31/665; A61K 31/4709; A61K 31/65; A61K 31/7088; A61K 31/16; A61K 31/7048
See application file for complete search history.

(56) References Cited

U.S. PATENT DOCUMENTS

| | | |
|---|---|---|
| 5,217,493 A | 6/1993 | Raad et al. |
| 5,407,670 A | 4/1995 | Shinault |
| 5,641,514 A | 6/1997 | Cho |
| 5,753,702 A | 5/1998 | Bednar et al. |
| 5,795,563 A | 8/1998 | Kallick |
| 5,902,283 A | 5/1999 | Darouiche et al. |

(Continued)

FOREIGN PATENT DOCUMENTS

| | | |
|---|---|---|
| CA | 2411944 A1 | 12/2001 |
| CA | 2489411 A1 | 1/2004 |

(Continued)

OTHER PUBLICATIONS

Alexander et al., Updated Recommendations for Control of Surgical Site Infections, Annals of Surgery Jun. 2011; 253(6):1082-1093.

(Continued)

*Primary Examiner* — Yong S. Chong
(74) *Attorney, Agent, or Firm* — Schwegman Lundberg & Woessner, P.A.

(57) ABSTRACT

Use of a pharmaceutical composition for the local treatment or prevention of a tissue infection at an infection site, the pharmaceutical composition comprising at least two different antibiotics of group A or pharmaceutically acceptable derivatives thereof, or an antibiotic of group A and at least one antibiotic of group B or pharmaceutically acceptable derivatives thereof. Group A comprises primarily intracellular active antibiotics working as inhibitor of bacterial RNA polymerase; as inhibitor of gyrase; or as inhibitor of bacterial protein synthesis. Group B comprises primarily extracellular active antibiotics working as inhibitor of bacterial cell wall synthesis; or inhibitor of bacterial protein synthesis; or by direct destabilization or rupture of the bacterial cell wall.

17 Claims, 12 Drawing Sheets

(56) References Cited

U.S. PATENT DOCUMENTS

| | | |
|---|---|---|
| 5,955,578 A | 9/1999 | Pierschbacher et al. |
| 6,270,347 B1 | 8/2001 | Webster et al. |
| 6,468,967 B1 | 10/2002 | Oleson, Jr. et al. |
| 6,475,434 B1 | 11/2002 | Darouiche |
| 6,680,308 B1 | 1/2004 | Hassan |
| 6,696,412 B1 | 2/2004 | Kelleher et al. |
| 6,812,224 B2 | 11/2004 | Jomaa |
| 6,887,270 B2 | 5/2005 | Miller et al. |
| 8,921,365 B2 | 12/2014 | Duewelhenke |
| 2003/0055022 A1 | 3/2003 | Bonner et al. |
| 2003/0065377 A1 | 4/2003 | Davila et al. |
| 2003/0153983 A1 | 8/2003 | Miller et al. |
| 2003/0194445 A1 | 10/2003 | Kuhner et al. |
| 2003/0224033 A1 | 12/2003 | Li et al. |
| 2004/0022824 A1 | 2/2004 | Li et al. |
| 2004/0077601 A1 | 4/2004 | Adams et al. |
| 2004/0131628 A1 | 7/2004 | Bratzler et al. |
| 2004/0249441 A1 | 12/2004 | Miller et al. |
| 2005/0079200 A1 | 4/2005 | Rathenow et al. |
| 2005/0161859 A1 | 7/2005 | Miller et al. |
| 2006/0051867 A1 | 3/2006 | Hamilton et al. |
| 2006/0127444 A1 | 6/2006 | Kuhn et al. |
| 2006/0171895 A1 | 8/2006 | Bucay-Couto |
| 2006/0171986 A1 | 8/2006 | Kuhn et al. |
| 2006/0188545 A1 | 8/2006 | Hadba |
| 2006/0210500 A1 | 9/2006 | Bicard-Benhamou et al. |
| 2006/0257444 A1 | 11/2006 | Tropsha et al. |
| 2006/0257445 A1 | 11/2006 | Tropsha et al. |
| 2006/0257446 A1 | 11/2006 | Tropsha et al. |
| 2007/0009564 A1 | 1/2007 | McClain et al. |
| 2007/0093894 A1 | 4/2007 | Darouiche |
| 2007/0125247 A1 | 6/2007 | Kunstmann et al. |
| 2007/0134287 A1 | 6/2007 | Troxel et al. |
| 2007/0142392 A1 | 6/2007 | Murphy et al. |
| 2007/0167380 A1 | 7/2007 | Dabre et al. |
| 2007/0191280 A1 | 8/2007 | Kelleher et al. |
| 2007/0243237 A1 | 10/2007 | Khaled et al. |
| 2008/0170991 A1 | 7/2008 | Shi et al. |
| 2008/0299202 A1 | 12/2008 | Marenzi et al. |
| 2009/0123515 A1 | 5/2009 | Taylor et al. |
| 2009/0318378 A1 | 12/2009 | Chaudhary |

FOREIGN PATENT DOCUMENTS

| | | |
|---|---|---|
| CA | 2490193 A1 | 1/2004 |
| CA | 2625004 A1 | 4/2007 |
| DE | 68926051 T2 | 8/1996 |
| DE | 19843383 A1 | 3/2000 |
| DE | 19859426 A1 | 7/2000 |
| DE | 10119096 A1 | 10/2002 |
| DE | 10227935 A1 | 1/2004 |
| DE | 202004009060 U1 | 8/2004 |
| DE | 10333098 A1 | 2/2005 |
| DE | 10333099 A1 | 2/2005 |
| DE | 102004060666 B3 | 3/2006 |
| DE | 102005002703 A1 | 7/2006 |
| EP | 1140952 A1 | 10/2001 |
| EP | 1147175 A2 | 10/2001 |
| EP | 1385449 A2 | 2/2004 |
| EP | 1462129 A1 | 9/2004 |
| EP | 1476205 A1 | 11/2004 |
| EP | 1526879 A2 | 5/2005 |
| EP | 1526880 A2 | 5/2005 |
| EP | 1680149 A1 | 7/2006 |
| EP | 1683531 A1 | 7/2006 |
| EP | 1718348 A2 | 11/2006 |
| EP | 1731142 A1 | 12/2006 |
| EP | 1884520 A2 | 2/2008 |
| EP | 1144592 A2 | 10/2008 |
| FR | 2546406 A1 | 11/1984 |
| GB | 1068587 A | 5/1967 |
| GB | 1530017 A | 10/1978 |
| GB | 2360789 A | 10/2001 |
| JP | 09183730 A | 7/1997 |
| RU | 2199978 C2 | 3/2003 |
| WO | 93/01841 A1 | 2/1993 |
| WO | 96/14859 A1 | 5/1996 |
| WO | 97/44024 A1 | 11/1997 |
| WO | 99/01089 A1 | 1/1999 |
| WO | 00/37477 A1 | 6/2000 |
| WO | 00/47716 A2 | 8/2000 |
| WO | 01/34128 A2 | 5/2001 |
| WO | 01/44271 A2 | 6/2001 |
| WO | 01/44274 A1 | 6/2001 |
| WO | 01/53330 A2 | 7/2001 |
| WO | 01/78799 A1 | 10/2001 |
| WO | 01/92288 A2 | 12/2001 |
| WO | 01/98297 A2 | 12/2001 |
| WO | 2001/95876 A1 | 12/2001 |
| WO | 02/32459 A2 | 4/2002 |
| WO | 03/061704 A2 | 7/2003 |
| WO | 03/066119 A1 | 8/2003 |
| WO | 03/082248 A2 | 10/2003 |
| WO | 2004/002479 A1 | 1/2004 |
| WO | 2004/002967 A1 | 1/2004 |
| WO | 2004/004661 A2 | 1/2004 |
| WO | 2004/010975 A2 | 2/2004 |
| WO | 2004/011055 A2 | 2/2004 |
| WO | 2004/066927 A2 | 8/2004 |
| WO | 2004/092283 A2 | 10/2004 |
| WO | 2005/042045 A1 | 5/2005 |
| WO | 2005/087135 A2 | 9/2005 |
| WO | 2005/110022 A2 | 11/2005 |
| WO | 2006/064516 A1 | 6/2006 |
| WO | 2006064517 A2 | 6/2006 |
| WO | 2006130629 A2 | 12/2006 |
| WO | 2007/002238 A2 | 1/2007 |
| WO | 2007/010584 A2 | 1/2007 |
| WO | 2007/011707 A2 | 1/2007 |
| WO | 2007/017019 A2 | 2/2007 |
| WO | 2007/022255 A2 | 2/2007 |
| WO | 2007/044693 A2 | 4/2007 |
| WO | 2007050565 A2 | 5/2007 |
| WO | 2008/030988 A2 | 3/2008 |
| WO | 2009/013024 A1 | 1/2009 |

OTHER PUBLICATIONS

Alt et al: "The effects of combined gentamicin-hydroxyapatite coating for cementless joint prostheses on the reduction of infection rates in a rabbit infection prophylaxis model", Biomaterials 27 (2006) 4627-4634.

Australian Examination Report dated Feb. 25, 2011 for Patent application AU2008280485.

Baddour et al., Update on Cardiovascular Implantable Electronic Device Infections and Their Management, A Scientific Statement From the American Heart Association, Circulation 2010; 121:458-477.

Bloom et al., Implantation Success and Infection in Cariovascular Implantable Electronic Device Procedures Utilizing an Antibacterial Envelope, PACE 2010; 1-10.

Boya P. et al: "Lysosomal membrane permeabilization induces cell death in a mitochondrion-dependent fashion", J Exp Med 197:10:1323-1334, May 19, 2003. Online at http://www.jem.org/cgi/doi/10.1084/jem.20021952.

Boyce et al: "Noncytotoxic combinations of topical antimicrobial agents for use with cultured skin substitutes", Antimicrobial Agents and Chemotherapy, Jun. 1995, vol. 39, No. 6, pp. 1324-1328.

Darouiche et al., A Comparison of Two Antimicrobial-Impregnated Central Venouse Catheters, The New England Journal of Medicine (ISSN 0028-4793) Jan. 7, 1999; 340:1-8.

Debbia et al: "In vitro activity of LY146032 alone and in combination with other antibiotics against gram-positive bacteria", Antimicrobial Agents and Chemotherapy, Feb. 1988, 32:2:279-281.

Edmiston, Jr, PHD et al., Is there an evidence-based argument for embracing an antimicrobial (triclosan)-coated suture technology to reduce the risk for surgical-site infections?: A meta-analysis, Surgery 2013; 154:89-100.

Ellington et al: "Intracellular *Staphylococcus aureus*: A mechanism for the indolence of osteomyelitis", J Bone Joint Surg (Br) 2003;85-B:918-921.

(56) References Cited

OTHER PUBLICATIONS

Espehaug et al: "Antibiotic prophylaxis in total hip arthroplasty. Review of 10,905 primary cemented total hip replacements reported to the Norwegian arthroplasty register, 1987 to 1995", J. Bone Joint Surg. [Br.] 1997;79-B:590-595.
Farber, B. F. et al: "Salicylic Acid Prevents the Adherence of Bacteria and Yeast to Silastic Catheters", Journal of Biomedical Materials Research, Wiley, New York, NY, US, vol. 27, No. 5, May 1993 (May 1993), pp. 599-602, XP009011038; ISSN: 0021-9304 (in English).
Fernandez-Valencia, Fosfomycin in Osteomyelitis. Chemotherapy 22:121-134 (1976).
Fournal et al., Meta-analysis of intraoperative povidone-iodine application to prevent surgical-site infection, British Journal of Surgery 2010; 97:1603-1613.
Friberg et al, Local Gentamicin Reduces Sternal Wound Infections After Cardiac Surgery: A Randomized Controlled Trial, Ann Thorac Surg 2005; 79:153-162.
Gatermann et al., The microbiological efficacy of the combination of fosfomycin and vancomycin against clinically relevant *Staphylococci*, Infection 17 (1989), Nr. 1, pp. 35-37.
Georgopoulos et al: "Aktivitaet von fosfomycin in kombination mit ampicillin, gentamicin, moxifloxacin, vancomycin and teicoplanin gegenaeber enterokokken mittels Biosreen-C-Analyzer", Antibiotika Monitor, vol. May 6, 2000, online at Http://www.ahc-net.at/001/antibiotika_monitor/56_00/56_8.htm. (with English abstract).
Ginalska et al: "Amikacin-loaded vascular prosthesis as an effective drug carrier", Internaitonal Journal of Pharmaceutics, Amsterdam, NL, vol. 339, No. 1-2, Jun. 28, 2007 (Jun. 28, 2007), pp. 39-46, XP022133352; ISSN: 0378-5173 (in English).
Grif et al: "In vitro activity of fosfomycin in combination with various antistaphylococcal substances", Journal of Antimicrobial Chemotherapy (2001) 48, pp. 209-217.
Hamilton-Miller: "In vitro activity of fosfomycin against 'problem' gram-positive cocci", Microbios 1992:71:95-103.
Harris et al: "*Staphylococci* and implant surfaces: a reciew", Injury, John Wright and Sons, Bristol, GB, vol. 37, No. 2, May 2006 (May 2006), pp. S3-S14; XP005411019; ISSN: 0020-1383 (in Enflish).
Hendriks et al: "Backgrounds of antibiotic-loaded bone cement and prosthesis-related infection," Biomaterials, vol. 25, No. 3, Feb. 2004, pp. 545-556.
International Search Report dated May 3, 2010 for PCT/EP2009/061682.
International Search Report for PCT/EP2008/006046, dated Nov. 19, 2008 and International Preliminary Report of Patentability for PCT/EP2008/006046, dated Nov. 19, 2008 and International Preliminary Report of Patentability for PCT/EP/006046, completed Oct. 26, 2009; ISA/IPEA/EP.
Jones et al: "Contemporary antimicrobial activity of triple antibiotic ointment: a multiphased study of recent clinical isolates in the United States and Australia", Diagn. Microbiol. Infect. Dis. 54 (2006) 63-71.
Kanellakopoulou et al: "Comparative elution of moxifloxacin from Norian skeetal repair system and acrylic bone cement; an in vitro study", International Journal of Antimicrobial Agents, Amsterdam, NL, vol. 28, No. 3, Sep. 2006 (Sep. 2006), pp. 217-220, XP005605464; ISSN: 0924-8579 (in English).
Kreft et al: "Experimental studies on nephrotoxicity and pharmacokinetics of LY 146032 (daptomycin) in rats", J. of Antimicrobial Chemotherapy, vol. 25, No. 4, 1990, pp. 635-644.
Krut et al: "Strain-specific association of cytotoxic activity and virulence of clinical *Staphylococcus aureus* isolates", Infection and Immunity, May 2003, 71: No. 5:2716-2723.
Lew, D. P. et al: "osteomyelitis" Lancet The, Lancet Limited, London, GB, vol. 364, No. 9831, Jul. 24, 2004 (Jul. 24, 2004), pp. 369-379, XP004747135; ISSN: 0140-6736 (in English).
Maathuis et al., Perioperative Contamination in Primary Total Hip Arthroplasty, Clinical Orthopaedics and Related Research 2005; 433:136-139.

Mangram, MD et al., Guideline for Prevention of Surgical Site Infection, 1999, Infection Control and Hospital Epidemiology Apr. 1999; 20(4):247-278.
Mauermann, MD et al., The anesthesiologist's Role in the Prevention of Surgical Site Infections, Anesthesiology Aug. 2006; 105(2):413-421.
McHugh et al, The role of topical antibiotics used as prophylaxis in surgical site infection prevention, J Antimicrob Chemother 2011; 66:693-701.
Mercuri et al: "Microbial Biofilms: A Potential Source for Alloplastic Device Failure", Journal of Oral and maxillofacial Surgery, Saunders, Philadelphia, PA, US, vol. 64, No. 8, Aug. 3006 (Aug. 2006), pp. 1303-1309, XP005559651; ISSN: 0278-2391 (in English).
Moreau et al: "Effectiveness of mupirocin and polymyxin B in experimental *Staphylococcus aureus*, Pseudomonas aeruginosa, and serratia marcescens keratitis," Cornea 21(8):807-811, 2002.
Morikawa et al: "Synergistic effect of fosfomycin and arbekacin on a methicillin-resistant *Staphylococcus aureus*—induce biofilm in a rat model", Int. J. of Antimicrobial Agents, vol. 25, 2005, pp. 44-50.
National Nosocomial Infections Surveillance (NNIS) System Report, data summary from Jan. 1992 through Jun. 2004, issued Oct. 2004, Am J Infect Control 2004; 32:470-485.
Norden, C. W. et al:, "Chronic Staphylococcal Osteomyelitis: Treatment with Regimens Containing Rifampin", Reviews of Infectious Diseases, Chicago, IL, US, vol. 5, No. Suppl 3, Jul. 1983 (Jul. 1983), pp. S495-S501, XP009041854 (in English).
Ochiai Minoru et al: "Clinical effect of arbekacin on MRSA infections after gastrointestinal surgery", Japanese Journal of Antibiotics, vol. 47. No. 6, 1994, pp. 837-843, XP009092459; ISSN: 0368-2781 (in Japanese and English).
Olay et al: Interaction of fosfomycin with other antimicrobial agents: in vitro and in vivo studies:, J. of Antimicrobial Chemotherapy, vol. 4, 1978, pp. 569-576.
Parvizi et al., Efficacy of antibiotic-impregnated cement in total hip replacement, A meta-analysis, Acta Orthopaedica 2008; 79(3):335-341.
Pistella et al., In vitro activity of fosfomycin in combination with vancomycin or teicoplanin against *Staphylococcus aureus* isolated from device-associated infections unresponsive to glycopeptide therapy, Infez Med (2) 2005, pp. 97-102.
Portier et al: "Treatment of severe staphylococcal infections with cefotaxime and fosfomycinin combination," Journal of Antimicrobial Chemotherapy, vol. 14, No. SupplB, Sep. 1984, pp. 277-284, Saunders Co. Ltd.
Quentin et al: In vitro activity of foxfomycin combined with rifampin, pefloxacin and imipenem against *Staphylococci*: A study by the time-kill curve method:, Drugs Exptl. Clin. Res. XIII(4), pp. 219-224 (1987).
Ramage, G. et al.Formation of Propionibacterium acnes biofilms on orthopaedic biomaterials and their susceptibility to antimicrobials, Biomaterials, Elsevier Science Publishers BV., Barking, GB, vol. 24, No. 19, Aug. 2003 (Aug. 2003), pp. 3221-3227, XP004425366; ISSN:0142-9612 (in English).
Ribes et al., Evaluation of fosfomycin alone and in combination with ceftriaxone or vancomycin in an experimental model of meningitis caused by two strains of cephalosporin-resistant *Streptococcus pneumoniae*, Journal of Antimicrobial Chemotherapy (2006) 57, pp. 931-936.
Rice et al: "In vitro synergism between daptomycin and fosfomycin against enterococcus faecialis Isolates with high-level gentamicin resistance", Antimicrobial Agents and Chemotherapy, vol. 33 (4), 1989, pp. 470-473.
Rice et al: "In vivo activity of the combination of daptomycin and fosfomycin compared with daptomycin alone against a strain of enterococcus faecalis with high-level gentamicin resistance in the rat endocarditis model", Diagn. Microbiol,. Infect. Dis., 1992; 15:173-176.
Richards et al: "Antiseptics and antiviotics on implants", Injury, John Wright and Sons, Bristol, GB, vol. 37, No. 2, May 2006 (May 2006), pp. S113-S116, XP005411033; ISSN: 0020-1383 (in English).

(56) References Cited

OTHER PUBLICATIONS

"U.S. Appl. No. 12/670,354, Advisory Action dated Jul. 23, 2013", 3 pgs.
"U.S. Appl. No. 12/670,354, Final Office Action dated Feb. 5, 2013", 11 pgs.
"U.S. Appl. No. 12/670,354, Final Office Action dated Apr. 4, 2014", 14 pgs.
"U.S. Appl. No. 12/670,354, Non Final Office Action dated Jul. 13, 2012", 13 pgs.
"U.S. Appl. No. 12/670,354, Non Final Office Action dated Sep. 26, 2013", 13 pgs.
"U.S. Appl. No. 12/670,354, Notice of Allowance dated Aug. 20, 2014", 9 pgs.
"U.S. Appl. No. 12/670,354, Pre-Brief Appeal Conference decision dated Aug. 8, 2014", 2 pgs.
"U.S. Appl. No. 12/670,354, Pre-Brief Conference request filed Jul. 7, 2014", 7 pgs.
"U.S. Appl. No. 12/670,354, Preliminary Amendment filed Jan. 22, 2010", 9 pgs.
"U.S. Appl. No. 12/670,354, Response filed Jan. 14, 2013 to Non Final Office Action dated Jul. 13, 2012", 15 pgs.
"U.S. Appl. No. 12/670,354, Response filed Mar. 26, 2014 to Non Final Office Action dated Sep. 26, 2013", 20 pgs.
"U.S. Appl. No. 12/670,354, Response filed Jun. 5, 2013 to Final Office Action dated Feb. 5, 2013", 17 pgs.
"U.S. Appl. No. 12/670,354, Response filed Jul. 6, 2012 to Restriction Requirement dated Jun. 8, 2012", 3 pgs.
"U.S. Appl. No. 12/670,354, Restriction Requirement dated Jun. 8, 2012", 6 pgs.
"European Application Serial No. 07075639.0, Extended European Search Report dated Dec. 21, 2007", 11 pgs.
"International Application Serial No. PCT/EP2008/006046, Written Opinion dated Nov. 19, 2008", 5 pgs.
Wahlig, "Lieber die Freisetzungskinetik von Antibiotika aus Knochenzementen -Ergebnisse vergleichender Untersuchungen in vitro and in vivo", Knochenzement: Werkstoff, klinische Erfahrungen, Weiterentwicklungen (W/ Machine Translation), (1987), 9 pgs.
Rodriguez et al., Synergic activity of fosfomycin in association with other antibacterial agents: A review. Drugs Exptl. Clin. Res. 1980, 6(4) pp. 281-288.
Rodriguez-Martineza et al: "P622 Penetration and activity of fosfomycin, ciprofioxacin, amoxicillin plus clayulanic acid and cotrimoxazol in *Escherichia coli* and Pseudomonas aeruginosa biofilms", International Journal of Antimicrobial Agents, Amsterdam, NL, vol. 29, Mar. 2007 (Mar. 2007), pp. S145-S146, XP022037815; ISSN: 924-8579 (in English).
Roessler et al: "Electrochemically assisted deposition of thin calcium phosphate coatings at near-physiological pH and temperature", Journal of Biomedical Materials Research, Part A, vol. 64A, Issue 4, pp. 655-663, 2003 Wiley Periodicals, Inc. Published online:Feb. 8, 2003: http://www3.interscience.wiley.com/cgi-bin/abstract/102530388/ Abstract.
Rutten et al., Prevention of Wound Infection in Elective Colorectal Surgery by Local Application of a Gentamicin-containing Collagen Sponge, Eur J Surg 1997: Suppl 578; 31-35.
Sanchez Andres et al: "Endocarditis neumococia: revision a proposito de un caso y nueva pauta de tratamiento asociada a fosfomicina", Acta Pediatrica Esp., 2007, vol. 65, No. 6, Jun. 2007, pp. 264-268.
Scheffer et al, Infections in orthopedics and traumatology: Pathogenesis and therapy, Der Orthopaede 2008, pp. 709-720. English abstract included.
Schiel et al: "Fosfomycin—ein Literaturueberblick", Antibiotika Monitor, vol. 1/2, 2005, pp. 8-25 (with English summary).
Schliephake et al: "Biological performance of biomimetic calcium phosphate coating of titanium implants in the dog mandible," Journal of Biomedical Materials Research, Part A, vol. 64 A, Issue 2, pp. 225-234, 2002, Wiley Periodicals, Inc. Published online: Dec. 18, 2002. Wiley InterScience: Journal: Abstract.
Senthi et al., Infection in total hip replacement: meta-analysis, International Orthopaedics (SICOT) 2011; 35:253-260.
Stallmann et al: "Antimicrobial peptides: review of their application in musculoskeletal infections", Injury, John Wright and Sons, Bristol, GB, vol. 37, No. 2, May 2006 (May 2006), pp. S34-S40, XP005411023; ISSN: 0020-1383 (in English).
Stratmann: "Die Biologie der Ansamycine: Beispiel Rifamycin", BIOspektrum, 3/04, Jahrgang 10, pp. 249-253 (English Abstract attached: "The Biology of Ansamycins: Example Rifamycin").
Trautmann et al: "Intracellular bactericidal activity of fosfomycin against *Staphylococci*: A comparison with other antibiotics", Infection 20 (1992) No. 6, pp. 48/350-52/354.
Tulkens P. And Andre Trouet: "The uptake and intracellular accumulation of aminoglycoside antibiotics in lysosomes of cultured rat fibroblasts", Biochem Pharmacol vol. 27:415-424, Feb. 15, 1978.
Wahlig, H., Ueber die Freisetzungskinetik von Antibiotika aus Knochenzementen—Ergebnisse vergleichender Untersuchungen in vitro und in vivo (About the release kinetics of antibiotics out of bone cements—results of comparative studies in vitro and in vivo). In: Willed, H.-G., Buchhorn, G. (Hrsg.), Aktuelle Probleme in der Chirurgie und Orthopaedie, Band 31, Knochenzement, 1987, 221-226 (with English translation of relevant portions).
Wahlig: "Ueber die Freisetzungskinetik von Antibiotika aus Knochenzementen—Ergebnisse vergleichender Untersuchungen in vitro und in vivo" Knochenzement: Werkstoff, klinische Erfahrungen, Weiterentwicklungen pp. 221-226. (About the release kinetice of antibiotics out of bone cements—results of comparative studies in vitro and in vivo), with English translation of relevant parts of article.
Zeitlinger, M. A et al: "Target site bacterial killing of cefpirome and fosfomycin in critically ill patients", International Journal of Antimicrobial Agents, vol. 21, No. 6, Jun. 2003 (Jun. 2003), pp. 562-567, XP002459419; ISSn: 0924-8579 (in English).
Zimmerli, MD et al., Prosthetic-Joint Infections, N Engl J Med Oct. 14, 2004; 351(16):1645-1654.

PHARMACEUTICAL COMPOSITION, SUBSTRATE COMPRISING A PHARMACEUTICAL COMPOSITION, AND USE OF A PHARMACEUTICAL COMPOSITION

CROSS-REFERENCE TO A RELATED APPLICATION

This application is a National Phase Patent Application of International Patent Application Number PCT/EP2008/006046, filed on Jul. 23, 2008, which claims priority of European Patent Application Number 07075639.0, filed on Jul. 23, 2007.

INTRODUCTION AND SUMMARY

The invention relates to the use of a pharmaceutical composition, a pharmaceutical composition, a pharmaceutical composition for treatment of extracellular and/or intracellular microbial infected cells, and a substrate comprising a pharmaceutical composition. The invention relates further to the use of antibiotics as anti-adhesives against microorganisms on surfaces.

Infections of bone and tissue are the severest problem of orthopedics and surgery, in particular due to increasing operation frequency. 30% of all bone infections become chronic despite of treatment. Further, many cases are known in which an infection reoccurred after alleged successful earlier treatment. In 3% of all cases, amputation is the only remaining option. Systemic treatment with antibiotics is difficult since antibiotics penetrate through bone generally only very poorly and thus concentrations being sufficiently high to eliminate an infection are hardly achievable.

Local application of antibiotics is better suited for therapy of infections of bone and other tissue than systemic antibiotic therapy since by local application higher concentrations of antibiotics can be achieved at the treatment site than by systemic application. A prerequisite for a successful local antibiotics therapy is a preceding radical surgical therapy, including debridement of all bone or tissue necroses and excision of all foreign material. Local antibiotics carrier known from prior art are bone cements made from polymethylmethacrylate (PMMA), beads made from PMMA, collagen fleeces and bone substituents. These carriers are commercially available with a limited number of antibiotics applied onto them: gentamicin, tobramycin, clindamycin, vancomycin and teicoplanin.

Though local antibiotics therapy employing the above-mentioned antibiotics have already improved treatment of bone and joint infections, such therapy fails in a significant number of cases (up to 16%). Therapy failure, however, often finally leads to the necessity of an amputation.

The major reasons for therapy failure are a) resistances against certain antibiotics, b) ineffectiveness of antibiotics against sessile bacteria, c) intracellular localised bacteria and d) induction of Small Colony Variants. In this context, ineffectiveness according to item b) is due to biofilm formation and cessation of proliferation of the bacteria to be eliminated. Further, in this context, intracellular is to be understood with respect to a cell of the host, i.e. of the subject to be treated. Thus, if bacteria are inside a cell of the host, antibiotics being unable to penetrate to the inner of the cell cannot act on the bacteria to be eliminated.

It has been known for some time that Staphylococci can survive inside leucocytes. Further, it is known that strains of *Staphylococcus aureus* showing the so-called Small Colony Variant phenotype can be internalised by keratinocytes and endothelial cells and can persist intracellularly. It was demonstrated that they remain intracellularly inside lysosomes. *S. aureus* of normal phenotype can also be internalised by endothelial cells, fibroblasts and keratinocytes and can remain intracellularly inside lysosomes.

It was demonstrated that *S. aureus* isolates display a dichotomy: Whereas cytotoxic strains survive in keratinocytes and fibroblasts and induce significant cytotoxicity to their host cells due to intracellular division, non-cytotoxic strains are killed inside of keratinocytes and fibroblasts, indicating that uptake of *S. aureus* represents an important mechanism of cell-autonomous host defence (Krut, O. et al., Infection and Immunity, 2003, 71: 2716-2723).

*S. aureus* can also be internalized by osteoblasts, but osteoblasts cannot kill internalized non-cytotoxic staphylococci, instead they can persist over days and weeks inside osteoblasts without proliferation. After lysis of the osteoblasts, the Staphylococci can proliferate again. Intracellular persistence of Staphylococci and possibly other bacteria in osteoblasts and their potential to persist intracellularly inside lysosomes may play a particular role when looking at bone infections. This could be causative for chronic progression of bone infections.

Though it is still not known exactly whether pseudomonades, streptococci and enterococci can persist in osteoblasts, intracellular persistence of these bacteria could be shown in general. This intracellular persistence was hitherto only thought to be possibly related with chronic progression of other diseases, but since pseudomonades, streptococci and enterococci are frequent pathogens with respect to bone infections, their intracellular persistence might be causative for chronic progression of bone infections.

Based on this assumption, it is explainable why allegedly successfully treated bone infections can re-outbreak even after years. Inside a host cell the bacteria are protected against numerous antibiotics which cannot penetrate the cell membrane (e. g. penicillins, glycopeptides). Though an acute infection being induced by planktonic (floating) bacteria might be treated with these antibiotics, bacteria can remain intracellularly and cause a re-infection after release from the host cell.

In prior art, bone and soft tissue infections are treated locally mainly with aminoglycosides (gentamicin, tobramycin) which usually cannot penetrate the cell membrane of host cells. On the other hand, it was reported that aminoglycosides can accumulate in lysosomes of fibroblasts but are inactive due to the low pH of lysosomes.

Consequently, antibiotics used in prior art for local therapy of infections of bone and other tissue are not suited to treat all these infections successfully. In particular, local antibiotics carrier containing only gentamicin are ineffective against infections of bacteria showing a Small Colony Variant phenotype and can even induce formation of Small Colony Variant phenotypes. None of the antibiotics used at present for local therapy of infection can eliminate intracellular localized bacteria.

WO 2006/064517 discloses an antibiotic composition comprising a first antibiotic inhibiting the bacterial protein synthesis and a second antibiotic not inhibiting the bacterial protein synthesis.

U.S. Pat. No. 5,217,493 discloses an implantable medical device which is coated against biofilm colonization with rifampin and novobiocin, or rifampin and minocycline.

Given an embodiment it is possible to provide a pharmaceutical composition for treating and preventing extra- and intracellular infections of cells, especially tissue cells, a substrate carrying such composition, and a method of applying such a composition and substrate.

It is further possible to decrease the adhesion rate of microorganisms on different substrate surfaces.

In an embodiment of the invention, the local treatment and prevention is done at an infection site. The tissue to be treated can e.g. be soft tissue and/or bone tissue including what is generally denoted as "bone". The pharmaceutical composition comprises at least two different antibiotics of group A or pharmaceutically acceptable derivatives thereof, or an antibiotic of group A and at least one antibiotic of group B or respective pharmaceutically acceptable derivatives thereof. Group A comprises primarily intracellular active antibiotics working as inhibitor of bacterial RNA polymerase, as inhibitor of gyrase or as inhibitor of bacterial protein synthesis. Group B comprises primarily extracellular active antibiotics working as inhibitor of bacterial cell wall synthesis or as inhibitor of bacterial protein synthesis or destabilise or rupture the bacterial cell wall directly.

In the context of the present description a tissue infection is understood as an extracellular and intracellular infection of tissue cells caused by microorganisms.

In order to circumvent resistances against the antibiotics used, particularly in long-term treatments, a combination of at least two antibiotics can be chosen. Such a combination results also in higher efficacy. Though it is generally considerable to use only intracellular active antibiotics, a combination of an intracellular active antibiotic (group A) with an extracellular active antibiotic (group B) may also be chosen. Though antibiotics of group B are not intracellular active, they can inhibit formation of resistances since they act on extracellular bacteria in a bactericidal manner and resistances are only formed in planktonic, proliferating populations of bacteria. Since the extracellular active antibiotics of group B show a different mechanism of action than the antibiotics of group A, parallel resistances can hardly occur.

The pharmaceutical composition to be used can comprise further additives, dispersants, solvents or carrier substances etc. known per se.

In order to achieve good results in treating infections of bone and other tissue, at least one of the antibiotics chosen should, in an embodiment, fulfil at least one of the following criteria:
a) It should penetrate the cell membrane of the host cell (i. e. the cell of the subject to be treated inside which the bacteria to be eliminated are located).
b) It should be able to reach the inside of the lysosomes of the host cell.
c) It should be active at low pH (particularly at that pH being present in lysosomes, i. e. ca. pH 4 to pH 5).
d) It should have a bactericidal activity.
e) It should show its bactericidal activity also against non-proliferating bacteria.

In an embodiment at least one of the antibiotics chosen fulfils a plurality of the criteria mentioned above. In another embodiment, fulfilment of all of these criteria is achieved. In still another embodiment, a fulfilment of all criteria by all antibiotics chosen is achieved.

In an embodiment said antibiotics of group A working as inhibitor of bacterial RNA polymerase comprise ansamycins, particularly rifamycins. Particularly, rifampin, rifabutin, rifapentine or rifamixin may be chosen. A pharmaceutical composition containing rifampin is particularly suited in eliminating intracellular Staphylococci, which were shown to be eliminated within 3 days after local administration of an according pharmaceutical composition.

In a further embodiment said antibiotics of group A working as inhibitor of gyrase comprise fluoroquinolones. The fluoroquinolone moxifloxacin is particularly chosen.

In an embodiment said antibiotics of group A working as inhibitor of bacterial protein synthesis comprise streptogramins like, e. g., quinupristin or dalfopristin. In an embodiment, a combination of quinupristin and dalfopristin is used. It is to be noted that the pharmaceutical composition to be used may contain more than a single antibiotic of each group (and more than two antibiotics of group A if no antibiotic of group B is used) and thus more than two antibiotics in total.

In an embodiment said antibiotics of group B working as inhibitor of bacterial cell wall synthesis or destabilising and rupturing the cell wall directly comprise glycopeptides, fosfomycin and polypeptides. In an embodiment the glycopeptides chosen are vancomycin and teicoplanin. In the same or another embodiment the polypeptides chosen are bacitracin, polymyxin B as well as other polymyxins and daptomycin.

In an embodiment said antibiotics of group B working as inhibitor of bacterial protein synthesis comprise aminoglycosides. In this context, particularly arbekacin may be chosen.

An exemplary pharmaceutical composition to be used comprises a rifamycin and an aminoglycoside. Another exemplary pharmaceutical composition comprises rifampin and arbekacin; such a composition essentially covers the entire germ spectrum to be eliminated and is effective against problematic bacteria like methicillin-resistant *S. aureus* (MRSA) or methicillin-resistant *S. epidermidis* (MRSE). Both antibiotics are effective also against non-proliferating (resting) bacteria and are temperature resistant (heat stable) so that they can be added to a bone cement made of poly(methylmethacrylate) (PMMA), to PMMA bead chains, and to spacers for revision operations.

Another pharmaceutical composition to be used comprises a rifamycin and fosfomycin. Still another pharmaceutical composition comprises rifampin and fosfomycin; such a composition also essentially covers the entire germ spectrum to be eliminated and is also effective against problematic bacteria like MRSA and MRSE. Fosfomycin has the further property that it binds reversibly to hydroxyl apatite and thus remains, even after release from a carrier, longer in a bone than other antibiotics. Further, fosfomycin is the smallest antibiotic known and diffuses or penetrates very well through or into bone tissue.

A further pharmaceutical composition to be used comprises a rifamycin and a fluoroquinolone. Another pharmaceutical composition comprises rifampin and moxifloxacin.

One object is also addressed by providing a pharmaceutical composition. Such a pharmaceutical composition can be used for the local treatment and prevention of a tissue infection at an infection site, whereby further embodiments of such a use are analogous to those explained above and to which in entirety reference is made hereby.

Such a pharmaceutical composition comprises at least two different antibiotics of group A' or pharmaceutically acceptable derivatives thereof, or an antibiotic of group A' and an antibiotic of group B' or pharmaceutically acceptable derivatives thereof. In this case, group A' comprises the primarily intracellular active antibiotics ansamycins, particularly rifamycins such as rifampin, rifabutin, rifapentine or rifamixin; fluoroquinolones, particularly moxifloxacin; streptogramins, particularly quinupristin and/or dalfopristin. Group B' comprises the primarily extracellular active antibiotics glycopeptides, particularly vancomycin or teicoplanin; fosfomycin; polypeptides, particularly bacitracin, daptomycin, or polymyxin B; and aminoglycosides, particularly arbekacin. It is to be noted that glycopeptides cannot be the second antibiotic of a pharmaceutical composition comprising only two antibiotics and comprising an ansamycin as first antibiotic.

In an embodiment the pharmaceutical composition comprises only a glycopeptide, a polypeptide or fosfomycin as possible antibiotic of group B', but no aminoglycosides are used as antibiotic of group B'. In another embodiment no streptogramins are used as antibiotic of group A'.

In an embodiment the antibiotics are chosen in such a way that either none or all antibiotics in the pharmaceutical composition work as inhibitors of protein synthesis, i.e. either a) only different streptogramins, or a streptogramin and an aminoglycoside may be used or b) no streptogramins and no aminoglycosides may be used at all.

In an alternative embodiment the pharmaceutical composition comprises a rifamycin and an aminoglycoside, particularly rifampin and arbekacin.

In another embodiment the pharmaceutical composition comprises a rifamycin and fosfomycin, particularly rifampin and fosfomycin.

Such a composition comprises rifamycin and fosmycin in such a concentration that the rifamycin reaches a concentration of 0.005 to 100 µg/ml, preferably 0.006 to 80 µg/ml, most preferably 0.0075 to 20 µg/ml at the site to be treated. Fosfomycin reaches a concentration of 1 to 1000 µg/ml, preferably 5 to 800 µg/ml, most preferably 10 to 200 µg/ml at the site to be treated.

In yet another embodiment the pharmaceutical composition comprises a rifamycin and polypeptide, particularly rifampin and daptomycin.

Such a composition comprises rifamycin and daptomycin in such a concentration that the rifamycin reaches a concentration of 0.005 to 100 µg/ml, preferably 0.006 to 80 µg/ml, most preferably 0.0075 to 20 µg/ml at the site to be treated. Daptomycin reaches a concentration of 0.1 to 100 µg/ml, preferably 0.5 to 80 µg/ml, most preferably 1 to 20 µg/ml at the site to be treated.

In still another embodiment the pharmaceutical composition comprises a rifamycin and a fluoroquinolone, particularly rifampin and moxifloxacin.

One object is also achieved by a pharmaceutical composition for the treatment of extracellular and/or intracellular microbial infected cells and/or for the prevention of microbial infections of cells comprising at least one antibiotic acting as an inhibitor of bacterial RNA polymerase, at least one antibiotic affecting the bacterial cell wall or its synthesis, and/or at least one antibiotic acting as a gyrase inhibitor.

The treatment preferably occurs locally or systemically.

Advantageously, ansamycins, particulary rifamycins such as rifampin, rifabutin, rifapentine or rifamixin are used as inhibitors of bacterial RNA polymerase. As antibiotics affecting the bacterial cell wall or its synthesis glycopeptides, particularly vancomycin or teicoplanin, fosfomycin and polypeptides, particularly bacitracin and daptomycin are chosen. As a gyrase-inhibitors fluoroquinolones, particularly moxifloxacin, is applied.

Rifamycin is used in concentrations between 0.005 to 100 µg/ml, preferably 0.006 to 80 µg/ml, most preferably 0.0075 to 20 µg/ml. Fosfomycin is used in concentrations of 1 to 1000 µg/ml, preferably 5 to 800 µg/ml, most preferably 10 to 200 µg/ml. Moxifloxacin is applied in a concentration between 0.1 to 500 µg/ml, preferably 0.5 to 200 µg/ml, most preferably 1 to 100 µg/ml. Daptomycin is used in concentrations of 0.1 to 100 µg/ml, preferably 0.5 to 80 µg/ml, most preferably 1 to 20 µg/ml. The same concentrations are preferably used in a combination of rifamycin, fosfomycin, daptomycin and/or moxifloxacin.

The pharmaceutical composition is especially effective in case of infected cells such as osteoblasts, leucocytes, erythrocytes, keratinocytes, fibroblasts, fat cells, muscle cells and/or endothelial cells.

Furthermore, the pharmaceutical composition is effective against microbial infection caused by gram-negative and/or gram-positive bacteria, preferably by the Staphyloccoci type, most preferably by *Staphylococcus aureus*.

In an embodiment the pharmaceutical compositions to be used further comprise a biofilm formation inhibitor. Every substance reducing or inhibiting at least partially the attachment of germs, especially bacteria on a surface or the ability of germs to accumulate on a surface to form a biofilm on that surface is considered as biofilm formation inhibitor.

In an embodiment salicylic acid or a pharmaceutical active derivative or salt thereof is used as biofilm formation inhibitor. Particularly, a combination of salicylic acid and an aminoglycoside may be used. Salicylic acid enhances the microbial activity of aminoglycosides against bacteria, especially against *E. coli* and *Klebsiella pneumoniae*: Salicylates enter a cell in a protonated form, thereby increasing the membrane potential of the cell. This, in turn, simplifies the uptake of aminoglycosides into the interior of the cell.

Even salicylic acid itself shows an effect on bacteria. Growth of encapsulated *Klebsiella pneumoniae* in the presence of salicylate results in reduced synthesis of capsular polysaccharides. The loss of capsular material exposes the cell surface of *K. pneumoniae* to the host defence mechanisms, thus shortening the time required for infection clearance. Salicylic acid reduces the ability of bacteria to adhere onto surfaces and to form biofilms. Though salicylic acid does not provide 100% protection against biofilm formation, it supports the effect of antibiotics.

Acetylsalicylic acid and/or its predominant metabolite salicylic acid exhibit definable impacts both in vitro and in vivo on microbial virulence phenotypes. Bacterial virulence factors help mediate infection by bacteria in a host organism. The following effects have been noted: reduction of adhesion to relevant biomatrices, reduction of capsule production, mitigation of biofilm formation, and diminution of vegetation growth, intravegetation bacterial proliferation, and hematogenous dissemination in experimental infective endocarditis. Salicylic acid also regulates positively the translation of specific gene loci including multiple antibiotic-resistance loci. Further, it induces cytoplasmic proteins; and increases quinolone resistance.

The synthesis of some types of fimbriae in *E. coli* e.g. colonization factor antigen, P fimbriae and type 1 fimbriae are reduced following growth in the presence of salicylate. Because fimbriae play a critical role in the attachment of *E. coli* to epithelial surfaces, salicylate treatment might prevent infection caused by some strains of fimbriated *E. coli*. Salicylate also limits adherence of *E. coli* to silastic catheters.

Chemotaxis in bacteria is modulated through regulation of flagella rotation. This rotation, when counterclockwise, leads to swimming along a linear trajectory and, when clockwise, leads to tumbling. Salicylate is recognized as a chemorepellant by the *E. coli* tsr gene product. This recognition leads to prolonged tumbling of motile *E. coli* and ultimately causes cells to migrate away from salicylate. Swarming behaviour of *E. coli* is also inhibited by salicylate in a concentration-dependent manner. Production of the flagellum itself in *E. coli* is inhibited by growth in the presence of salicylate. This is mediated by inhibiting the production of flagellin, the protein monomer constituting the flagella. It has also been speculated that inhibition of flagella synthesis and motility in *E. coli* by salicylate is due to reduced synthesis in OmpF synthesis, which may be required for flagella assembly.

Biofilms consist of microorganisms and other matter encased in a polysaccharide matrix of microbial origin. Growth of *Pseudomonas aeruginosa* and *Staphylococcus epidermidis* in the presence of salicylate reduces the production of extracellular polysaccharide required for biofilm formation. The reduction in biofilm formation decreases the ability of these organisms to adhere to contact lenses and medical polymers. A component of biofilm production in *S. epidermidis* is extracellular slime which is composed of a complex mixture of polysaccharides, teichoic acids and proteins. Production of slime-associated proteins and teichoic acids is inhibited in *S. epidermidis* by salicylate.

In case of *S. aureus*, salicylic acid mitigates two distinct virulence phenotypes that are of key relevance for matrix binding, i.e. to fibrinogen and fibronectin, and α-hemolysin activity. These effects are specifically associated with salicylic acid-mediated reduction in the expression of the respective structural genes, i.e., fnbA, fnbB, and hla. In addition to the suppression of matrix protein binding and cytolytic profiles, enhanced exoenzyme and protein A production occurs in the presence of salicylic acid. These findings raise the likelihood that salicylic acid executed its antimicrobial effects through one or more global regulatory networks rather than a decrease in general gene transcription. Global regulon sarA and the global regulon agr are mitigated by salicylic acid, corresponding to the reduced expression in of the hla and fnbA genes in vitro. It should be noted that *S. aureus* virulence parameters were not completely suppressed by salicylic acid but were reduced, in a drug concentration-dependent manner, by a maximum of approximately 50%.

In an embodiment the infected tissue to be treated is acutely or chronically infected. A combination of an acute and a chronic infection, i.e. the acute infection overlying the chronic infection, might also be treated.

The object is also achieved by providing a substrate for medical purposes according to claim 21. The substrate is preferably used as carrier of the pharmaceutical composition when locally treating and preventing the tissue infection. In a further embodiment the substrate is also used locally after removal of the infected tissue as a supplement in surgical debridement.

In one embodiment the substrate can be soaked with the pharmaceutical composition to be used. In another embodiment the pharmaceutical composition can be dispersed in a base material of the substrate. In still another embodiment, the pharmaceutical composition can be polymerised with the base material. Thus, it is possible to coat the substrate with the pharmaceutical composition and/or to incorporate the pharmaceutical composition into the substrate.

In a preferred embodiment the substrate underwent special treatment e.g. sand blasting or hydroxyl apatite coating before the pharmaceutical composition is applied.

Within the scope of the present description is also a coating made of a support material in which the pharmaceutical composition is present e.g. in a dispersed form. Such support material can include polylactides. The support material with the dispersed pharmaceutical composition is then applied as a coating onto the substrate—either directly onto the surface of the latter or onto a layer being already present on that surface or on another layer.

In an embodiment the substrate comprises a fleece, a fabric, a polymethyl methacrylate, a copolymer of methylmethacrylate and methylacrylate, a resorbable polymer, polyethylene, a metal or a metal alloy e.g. a Ti6Al4V alloy or another titaniumium alloy, a ceramic, a bone cement, particularly made from a polymeric material or from calcium phosphate and/or a bone substitute. Thus, PMMA bead chains consisting mainly of a copolymer of methylmethacrylate and methylacrylate as well as glycine and a specific pharmaceutical composition to be administered as local antibiotics carrier are a possible substrate. Further, the bone cement may be intended to be used for spacer and for revision operations.

In case of PMMA bead chains, the following mode of use is possible: firstly, the pharmaceutical composition is dispersed within the PMMA base material. The powder is heated to 180° C. and filled into forms by injection moulding. The pharmaceutical composition is being distributed all over the base material and can diffuse from the inner parts of a PMMA bead towards the surface, where it may interact with bacteria being present around the PMMA bead chain. The PMMA bead chains may comprise 0.1-10 wt %, preferably 0.5-8 wt %, most preferably 1-5 wt % antibiotic(s).

In another embodiment, particularly in case of revision operations, the substrate is an implantable prosthesis, wherein joint prostheses and particularly knee, hip, shoulder, elbow prostheses as well as vertebral implants are respective examples. Furthermore, all implants for trauma surgery like screws, plate, etc. may be used as substrate. The substrate coating may comprise 10-1000 μg/cm$^2$, preferably 20-500 μg/cm$^2$, most preferably 50-300 μg/cm$^2$ antibiotic(s) per cm$^2$ substrate surface area.

In an embodiment the fleece or fabric comprises a natural or synthetic fibre, which can be biodegradable, wherein polylactide (polylactic acid) is an exemplary material. In another embodiment the fleece or fabric comprises collagen, wherein the fleece may consist essentially of collagen. In the latter case, the collagen fleece is also completely biodegradable. The fleece may comprise 0.01-10 mg/cm$^2$, preferably 0.1-8 mg/cm$^2$, most preferably 0.5-5 mg/cm$^2$ antibiotic(s) per cm$^2$ fleece.

Further a method for locally treating a subject with a pharmaceutical composition is described, the pharmaceutical composition comprising:
at least two different antibiotics of group A or pharmaceutically acceptable derivatives thereof or
an antibiotic of group A and at least one antibiotic of group B or pharmaceutically acceptable derivatives thereof, wherein
group A comprises intracellular active antibiotics working as
inhibitor of bacterial RNA polymerase,
inhibitor of gyrase or
inhibitor of bacterial protein synthesis and
group B comprises extracellular active antibiotics working
as inhibitor of bacterial cell wall synthesis,
as inhibitor of bacterial protein synthesis or
by direct destabilisation or rupture of the bacterial cell wall.

This method may be particularly used for treating a tissue infection of said subject, wherein the tissue may be, e.g., soft tissue and/or bone tissue and/or bone. These infections might occur due to a surgical operation, particularly due to an operation related to implanting an implant into a human or non-human body. Thus, the treatment might be applied to a human or non-human body.

With respect to further embodiments of this aspect reference is made the explanations given above which are analogously applicable for said method, particularly regarding the substrate to be used and the antibiotics to be chosen.

A second object is achieved by using a combination of at least antibiotic acting as an inhibitor of bacterial RNA polymerase and at least one antibiotic affecting the bacterial cell wall or its synthesis as anti-adhesives against microorganisms on surfaces.

The inhibitor of bacterial RNA polymerase is preferably selected from the group comprising ansamycins, particulary rifamycins such as rifampin, rifabutin, rifapentine or rifamixin.

The antibiotic affecting the bacterial cell wall or its synthesis is preferably selected from the group comprising glycopeptides, particularly vancomycin or teicoplanin, fosfomycin and polypeptides, particularly bacitracin or daptomycin. A preferred combination comprises rifamycin and fosfomycin.

In a further embodiment the microorganisms are gram-negative and/or gram-positive bacteria, preferably of the Staphyloccoci type, most preferably *Staphylococcus aureus*.

The combination of the at least one inhibitor of bacterial RNA polymerase and the at least one antibiotic affecting the bacterial cell wall or its synthesis is preferably attached or coated onto surfaces made of metal, preferably titanium, steel or metal alloy, ceramics, and bone cement or hydroxyl apatite.

When coated on a substrate the combination may comprise rifamycin and fosfomycin in a concentration between 10 and 1000 µg/cm$^2$, preferably 20 to 500 µg/cm$^2$, most preferably 50-200 µg/cm$^2$, respectively.

Advantageously, the antiadhesive effect is accompanied by a bactericidal effect on the tissue surrounding the coated surfaces.

BRIEF DESCRIPTION OF THE DRAWINGS

Examples of embodiments are explained in further detail by means of the following figures and examples.

DETAILED DESCRIPTION

Figure 1:
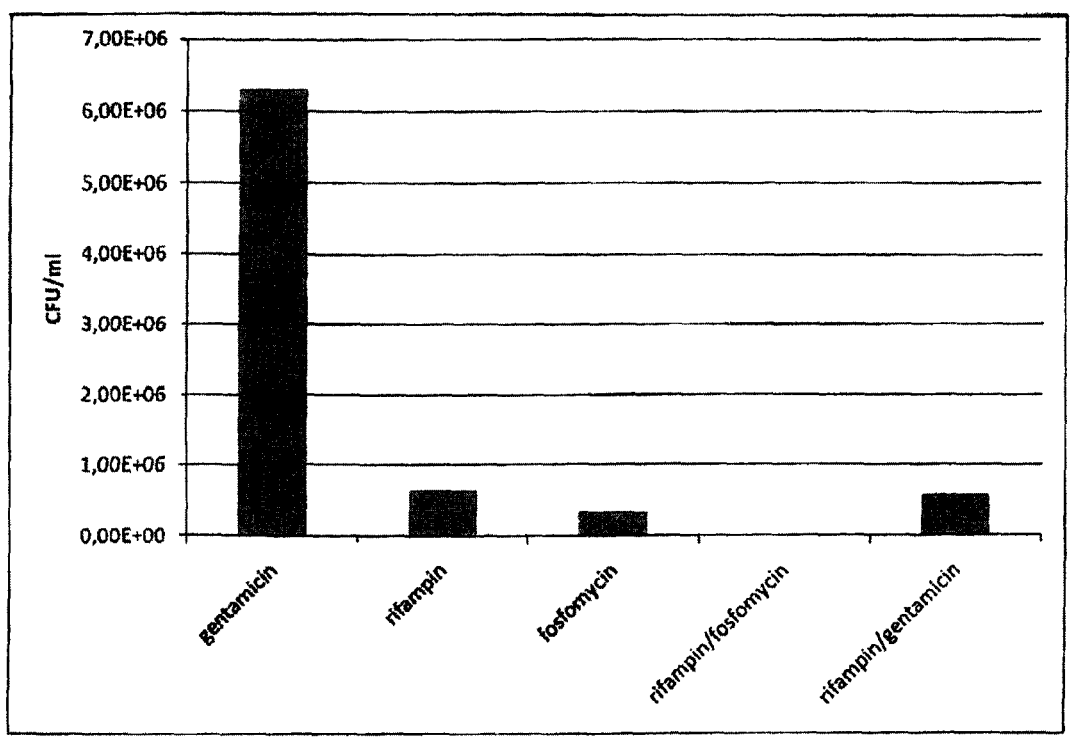
FIG. 1 shows CFU of *S.aureus* ATTC 6538P in cell culture supernatant of osteoblastic MG63 cells.

1. Use of Rifampin and Fosfomycin or their Combination for the Treatment of Extracellular Infections 1.1. Use of Rifampin and Fosfomycin or their Combination for the Treatment of Extracellular Infections of Osteoblastic MG63 Cells Infected with *Staphylococcus aureus* subsp. *aureus* Rosenbach (ATTC 6538P)

Osteoblastic MG63 cells were detached with the cell detachment medium Accutase 24 hours before infection. The cell number was determined using the Neubauer counting chamber. Cells were seeded onto uncoated 24 well plates with a cell density of $1.5 \times 10^4$ cells/cm$^2$ in 1 ml DMEM (Dulbecco's Modified Eagle's Medium) with 10% FCS (fetal calf serum), 1% Glutamax-I and 1% Natrium Pyruvat and incubated at 37° C. and 5% $CO_2$.

An overnight culture of *S.aureus* ATTC 6538P was prepared by infecting 5 ml Caso-Bouillon medium with *S.aureus* ATTC 6538P. The cultures were incubated with shaking (450 U/min) over night at 37° C. 100 µl of the overnight cultures were transferred into 5 ml Caso Bouillon medium and incubated for 2 h at 37° C. with shaking (450 U/min) prior to infection.

The cell culture supernatant of the osteoblastic MG63 cells was removed with a pipette from the wells. 1 ml containing $1 \times 10^6$ *S.aureus* ATTC 6538P cells was added to each well. Two 24 well plates were incubated with *S.aureus* ATTC 6538P. The combined osteoblastic cells and bacteria were incubated for 1.5 h at 37° C. under 5% $CO_2$ atmosphere. The presence of bacteria was determined using a microscope.

After 1.5 h the supernatant was removed and the wells were carefully washed twice with 37° C. warm DMEM without additives. It was microscopically checked, if not too many cells were detached during the washing procedure. During the washing only the planktonic cells were removed, bacteria adhered to cells and the cell culture plastics were visible in great numbers. Afterwards 1 ml of cell culture complete medium was added to each well containing following antibiotics:

100 µg/ml gentamicin
1 µg/ml rifampin
100 µg/ml fosfomycin disodium
1 µg/ml rifampin+100 µg/ml fosfomycin disodium
1 µg/ml rifampin+100 µg/ml gentamicin No negative control without antibiotics was used since the strong bacterial growth in absence of antibiotics would damage the osteoblastic cells.

After incubation for 24 h, 100 µl of the cell culture supernatant was streaked out on Caso agar plates (Casein-peptone soymeal-peptone broth) directly, e.g. in case of rifampin, fosfomycin, rifampin/fosfomycin and rifmpicin/gentamicin, or after appropriate dilution, e.g. 1:100 in case of gentamicin, and incubated overnight at 37° C. The supernatant of two wells per group was streaked out.

The person skilled in the art will recognize that the above given description is just one possibility out of many alternatives.

The CFU (colony forming unit) of the supernatant was determined and is shown in FIG. 1.

FIG. 1 shows clearly a sensitivity of *S.aureus* ATTC 6538P located in the culture supernatant of osteoblastic MG63 cells towards the different antibiotics with the exception of gentamicin Although the used concentrations were high compared to the MIC values (minimal inhibitory concentration) determined for this *S.aureus* strain, the bacteria could not be removed completely with the antibiotic treatment. This is due to the fact that the bacteria settled on the surface of the cells or the cell culture plastic, which results in reduced sensitivity to antibiotics. This simulates the in vivo situation where staphylococci readily bind to the extracellular matrix and foreign bodies. The effect of rifampin, fosfomycin and the combination of rifampin/gentamicin is moderate, whereas the combination rifampin/fosfomycin shows a strong, synergistic effect.

1.2. Use of Rifampin and Fosfomycin or their Combination for the Treatment of Extracellular Infections of Osteoblastic MG63 Cells Infected with *Staphylococcus aureus* subsp. *aureus* (BAA44)

The experimental set up for the infection of osteoblastic MG63 cells infected with *S.aureus* BAA44, a MRSA strain with additional resistance against multiple antibiotics, was basically the same as above.

Following antibiotics were used:
100 µg/ml vancomycin
10 µg/ml rifampin
100 µg/ml fosfomycin
10 µg/ml rifampin+100 µg/ml fosfomycin
10 µg/ml rifampin+100 µg/ml vancomycin.

After incubation for 24 h 100 µl of the cell culture were streaked out on Caso agar plates (Casein-peptone soymeal-peptone broth) directly, e.g. in case of vancomycin, rifampin/fosfomycin and rifampin/vancomycin, or after appropriate dilution, e.g. 1:100 in case of rifampin and fosfomycin, and incubated overnight at 37° C. The supernatant of two wells per group was streaked out.

The person skilled in the art will recognize that the above given description is just one possibility out of many alternatives.

Figure 2:
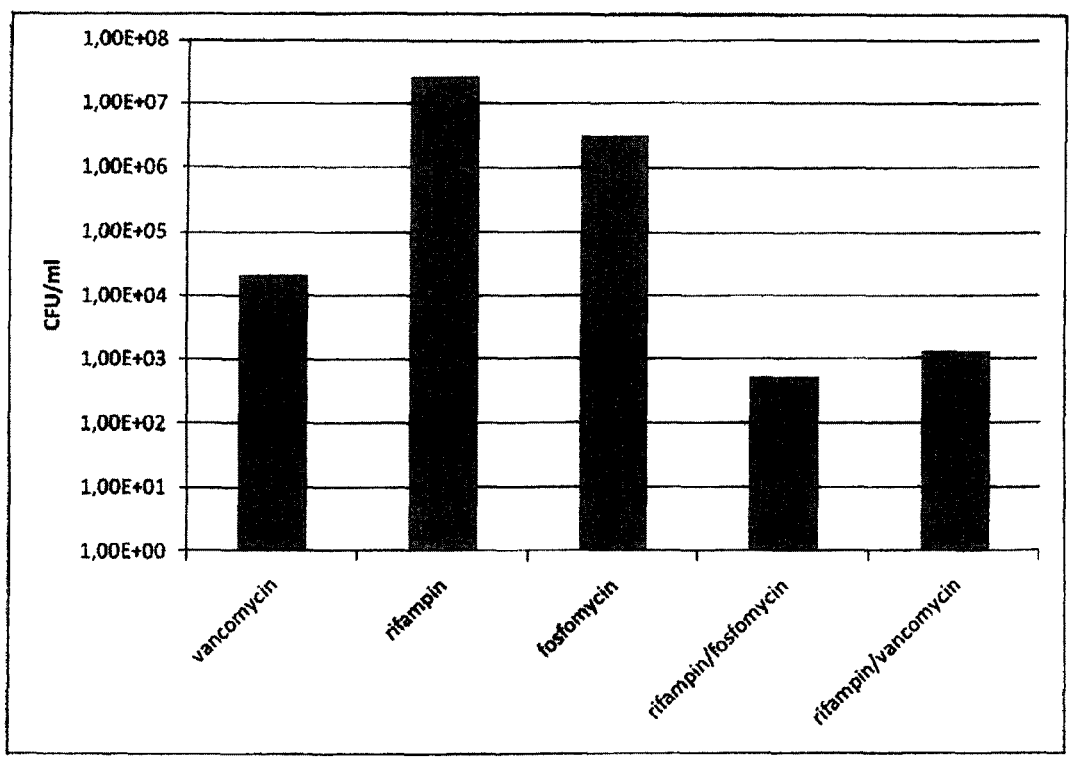
FIG. 2 shows CFU of *S.aureus* BAA44 in cell culture supernatant of osteoblastic MG63 cells.

The CFU (colony forming unit) of the supernatant was determined and is shown in FIG. 2.

FIG. 2 shows clearly a sensitivity of *S.aureus* BAA44 located in the culture supernatant of osteoblastic MG63 cells towards the different antibiotics. It is pointed out that it was necessary to adapt the CFU values logarithmical.

Rifampin in the used concentration shows as expected hardly any efficacy, since *S.aureus* BAA44 is a rifampin resistant strain. Also the antibiotic effect of fosfomycin is relatively small. However, the combination rifampin/fosfomycin shows a strong, synergistic effect on extracellular *S.aureus* BAA44, which was surprising and not expected due to the weak effect of the single compounds.

The effect of the combined rifampin/fosfomycin is even slightly better than the effect of vancomycin, which is one of the most important antibiotics for the treatment of MRSA infections. The combination of vancomycin and rifampin also shows a slight synergistic effect. It is noteworthy that the concentration of vancomycin used in this experiment was very high to increase the otherwise weak bactericidal effect of vancomycin. A concentration of 100 µg/ml vancomycin cannot be achieved with intravenous application.

2. Use of Different Antibiotics, i.e. Rifampin and fosfomycin or their Combination for the Treatment of Intracellular Infections 2.1. Use of Different Antibiotics, i.e. Rifampin and Fosfomycin or their Combination for the Treatment of Intracellular Infections of Osteoblasts MG63 Infected with *Staphylococcus aureus* subsp. *aureus* Rosenbach (ATTC 6538P)

The experimental set up for determination of intracellular infection of osteoblastic MG63 cells infected with *S.aureus* ATTC 6538P was essentially the same as above.

However, in order to eliminate extracellular *S.aureus* ATTC 6538P each cell culture was treated with lysostaphin after infection before adding the antibiotics.

For this purpose the bacterial suspension was removed from each well and the cells were washed once with warm DMEM containing 10% FCS. 250 µl 25 µg/ml lysostaphin solution was added to each well. The cells were incubated for 10 min at 37° C. Afterwards no extracellular bacteria could be observed microscopically. The lysostaphin solution was removed completely and the cells were washed once with 1 ml warm DMEM. Afterwards the antibiotic solutions having the following compositions were added:
100 µg/ml vancomycin
100 µg/ml gentamicin 0.01-100 µg/ml rifampin
10-1000 µg/ml fosfomycin
1 µg/ml rifampin+100 µg/ml fosfomycin
1 µg/ml rifampin+100 µg/ml gentamicin
1-100 µg/ml moxifloxacin The infected cells were incubated for 24 h at 37° C. under $CO_2$ atmosphere.

In order to determine the metabolic activity of osteoblastic MG63 cells after infection, the cell supernatant was removed and 1 ml of warm fresh cell culture medium was added to each well. Afterwards 200 µl of MTT solution (3[4,5-Dimethylthiazol-2-yl]-2,5-diphenaltetrazoliumbromide) was added to each well. The cultures were incubated for 2 h at 37° C. under 5% $CO_2$ atmosphere. The cell culture supernatant was removed and the formazan, which was formed due to metabolic activity, was solubilised with 1 ml isopropanol. 200 µl of each suspension were transferred to a 96 well microtiter plate and the absorbance at 540 nm was measured with an ELISA reader (Tecan).

The absorbance at 540 nm is an indicator for the metabolic activity of the osteoblastic MG63 cells. The intracellular propagation of the cytotoxic S.aureus strain ATTC 6538P in osteoblastic MG63 cells leads to the death of the infected cell. The lower the extinction is the lower is the metabolic activity of the cells and thus the stronger is the infection of the cells with S.aureus ATTC 6538P.

The person skilled in the art will recognize that the above given description is just one possibility out of many alternatives.

FIGS. 3 a-d show the influence of the different antibiotics on the metabolic activities of osteoblastic MG63 cells.

Vancomycin is unable to penetrate into the cell and thus does not influence the intracellular propagation of S.aureus inside the osteoblastic cells. Therefore, the metabolic activity of the osteoblastic cells is strongly reduced due to the infection with S.aureus ATTC 6538P (FIGS. 3a-d). The same applies to gentamicin. Nevertheless, in combination of gentamicin with rifampin the metabolic activity was higher than for rifampin alone (data not shown).

Figure 3A:
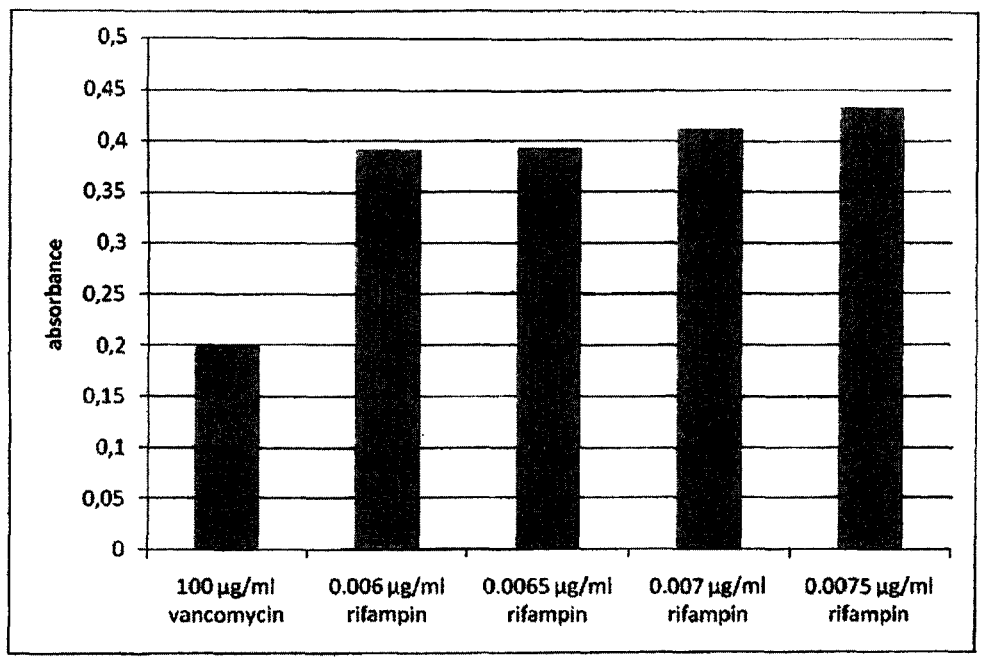
FIG. 3a shows metabolic activity of osteoblastic MG63 cells after infection with *S. aureus* ATTC 6538P followed by addition of rifampin to the cell culture supernatant after treatment with lysostaphin to remove extracellular bacteria.
Figure 3B:
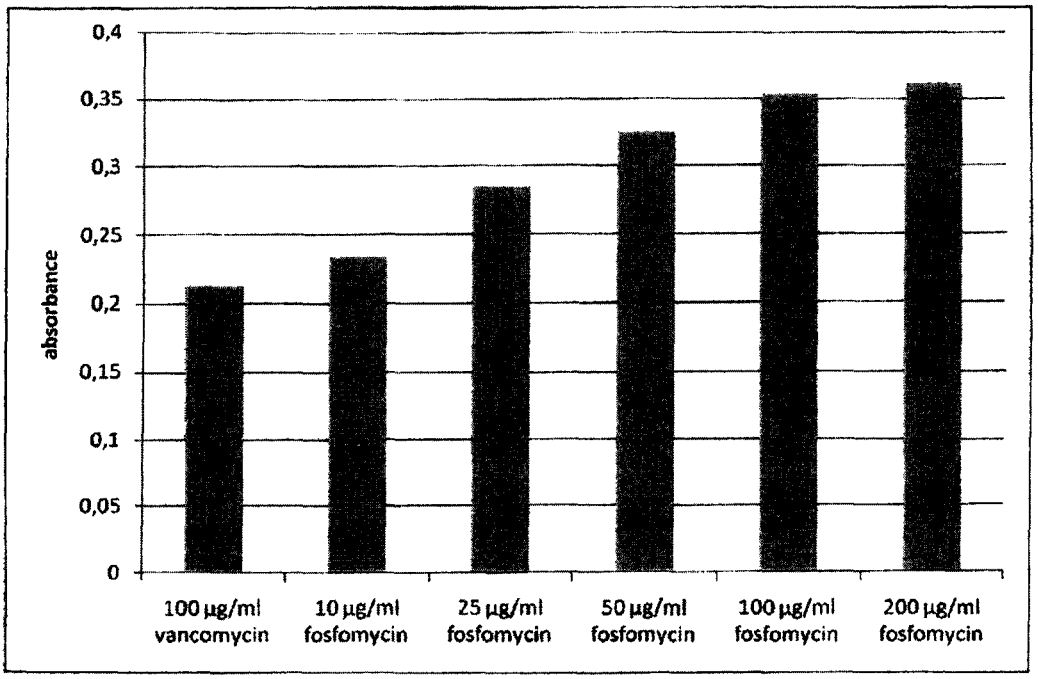
FIG. 3b shows metabolic activity of osteoblastic MG63 cells after infection with *S. aureus* ATTC 6538P followed by addition of fosfomycin to the cell culture supernatant after treatment with lysostaphin to remove extracellular bacteria.

Rifampin on the other hand is able to reduce the cell death caused by S.aureus ATTC 6538P drastically (FIG. 3a). Already small concentrations (0.006 µg/ml) are sufficient in increasing the metabolic activity.

Fosfomycin also influences the intracellular propagation of S.aureus ATTC 6538P and thus the metabolic activity of the infected osteoblastic cells (FIG. 3b). 10 µg/ml fosfomycin increases the metabolic activity only slightly, whereby 100 µg/ml had the maximal effect and almost doubled the metabolic activity. This result is surprising since so far it has not been known that fosfomycin is be able to penetrate into cells. It is only known that fosfomycin can penetrate into neutrophils.

Figure 3C:
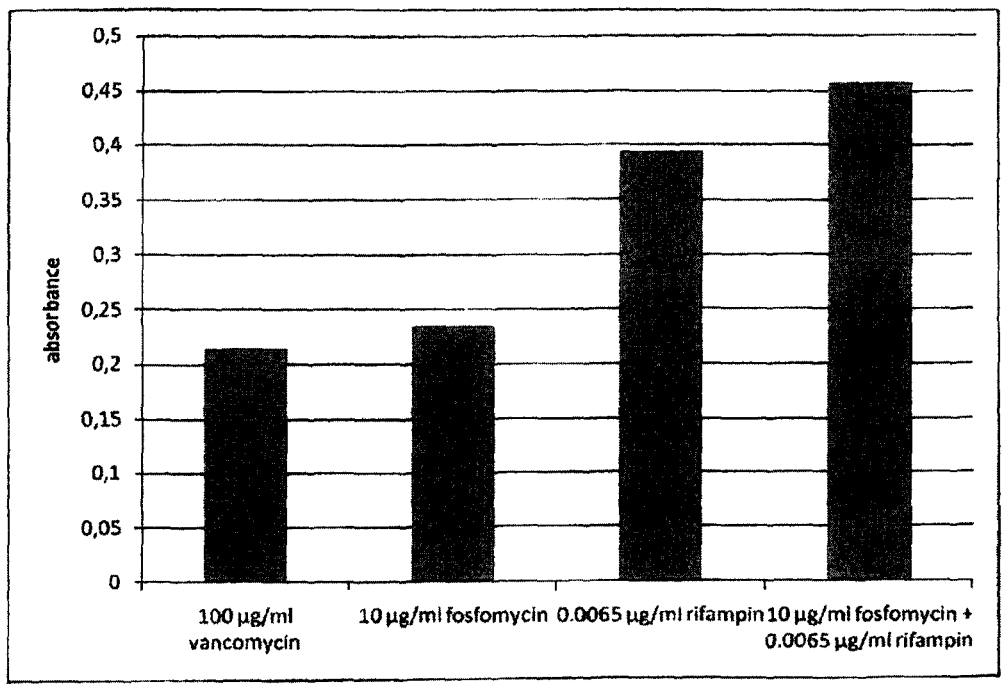
FIG. 3c shows metabolic activity of osteoblastic MG63 cells after infection with *S. aureus* ATTC 6538P followed by addition of fosfomycin, rifampin and their combination to the cell culture supernatant after treatment with lysostaphin to remove extracellular bacteria.
Figure 3D:
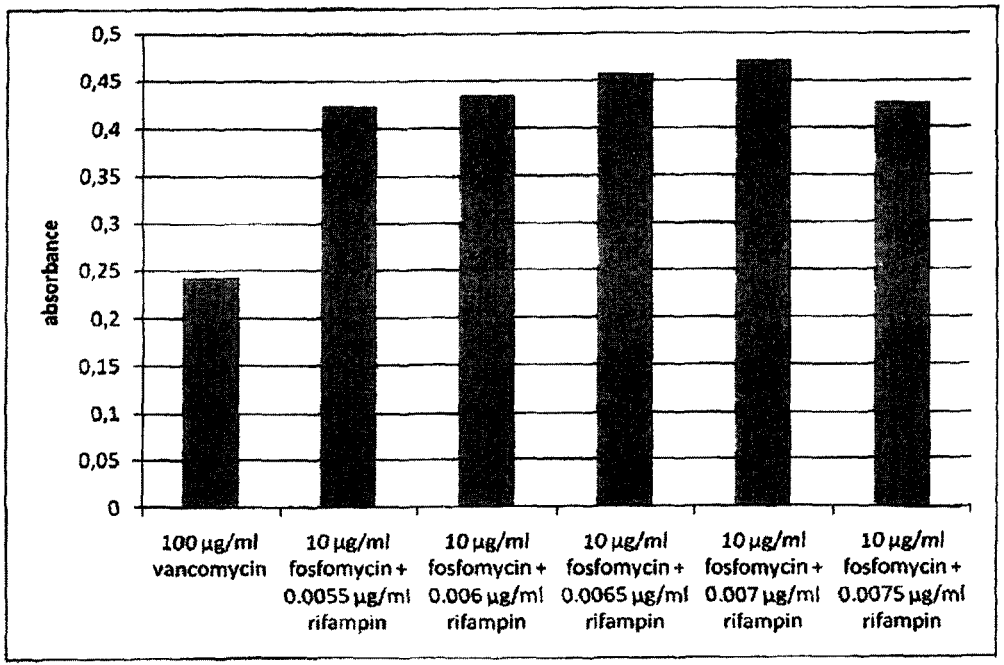
FIG. 3d shows metabolic activity of osteoblastic MG63 cells after infection with *S. aureus* ATTC 6538P followed by addition of after adding a mixture containing 10 µg/ml fosfomycin and 0.006-0.0075 µg/ml rifampin to the cell culture supernatant after treatment with lysostaphin to remove extracellular bacteria.

The combination of rifampin and fosfomycin also leads to an increase of metabolic activity (FIG. 3d), even showing a synergistic effect (FIG. 3c).

Figure 3E:
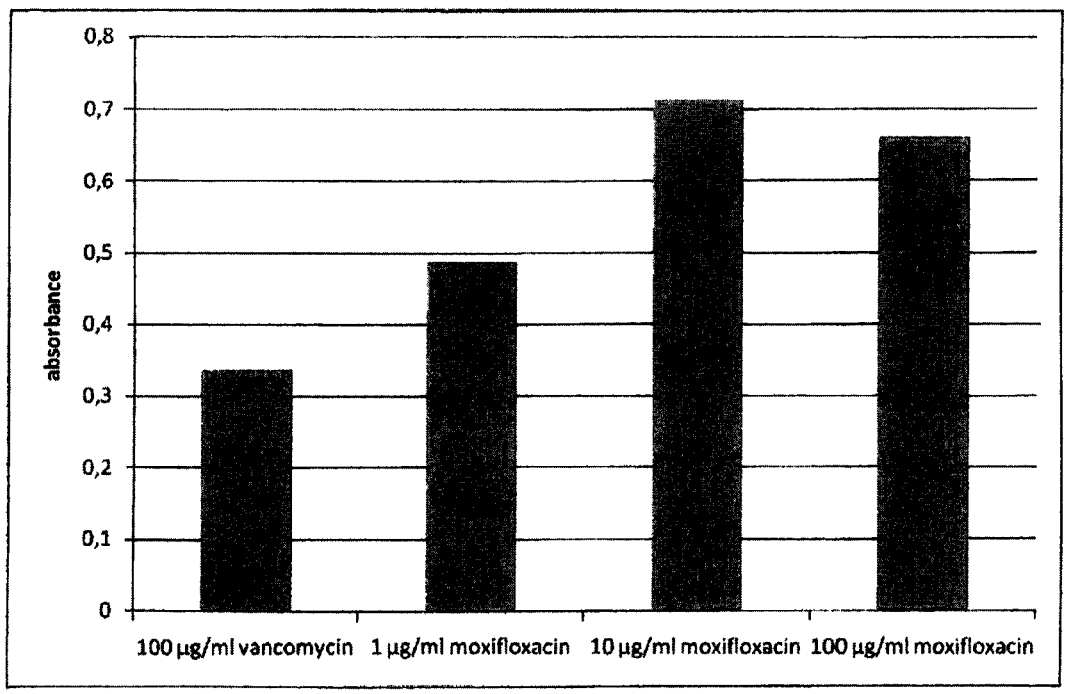
FIG. 3e shows metabolic activity of osteoblastic MG63 cells after infection with *S. aureus* ATTC 6538P followed by addition of moxifloxacin to the cell culture supernatant after treatment with lysostaphin to remove extracellular bacteria.

Also the application of 1 to 100 µg/ml moxifloxacin can inhibit intracellular growth of S.aureus ATTC 6538P and thus increase the metabolic activity up to more than two fold (FIG. 3e).

2.2. Use of Rifampin, Fosfomycin or their Combination for the Treatment of Intracellular Infections of Osteoblasts MG63 Infected with *Staphylococcus aureus* subsp. *aureus* (BAA44)

The experimental set up for determination of intracellular infection of osteoblastic MG63 cells infected with S.aureus BAA44 was essentially the same as above described for S.aureus ATTC 6538P.

Because the non-cytotoxic S.aureus BAA44 persists in osteoblasts and does not divide intracellularly like the cytotoxic strain S.aureus ATTC6538P, the intracellular localisation of S.aureus BAA44 does not result in cell death of the osteoblastic cells. The intracellular infection of the osteoblastic MG63 cells with S.aureus BAA44 could therefore not be determined on basis of the metabolic activity of the cells and was determined via cell lysis and counting of the intracellular CFU instead.

Antibiotic solutions having the following compositions were added:
100 µg/ml vancomycin
2.5-40 µg/ml rifampin
25-400 µg/ml fosfomycin
and their mixtures in different ratios as given below.

The infected cells were incubated with the antibiotics for 24 h at 37° C. under 5% $CO_2$ atmosphere.

Afterwards the cells are washed once with PBS pH 7.4 (phosphate buffer solution) followed by lysis with 1 ml 0.1% Triton X100 in ringer's solution. The lysates were treated for 5 min with ultrasound. The lysates are thoroughly resuspended with a pipette. Only one 24 well plate was handled and the other plates were stored at 4° C. in order to minimize bacterial growth in the lysate. 100 µl lysate were undiluted streaked out on Caso agar plates, incubated over night at 37° C. and the colonies were counted.

FIGS. 4a-4g show the CFU value per well as an indicator for the degree of intracellular S.aureus BAA44 infections of osteoblastic MG63 cells. The lower the CFU value is the lower is the infection rate of the osteoblastic cells with S.aureus BAA44. This correlates to the efficacy of the added antibiotic. Due to the weak intracellular growth of S. aureus BAA44, a decrease in CFU is caused by the bactericidal effect of the antibiotics.

Figure 4A:
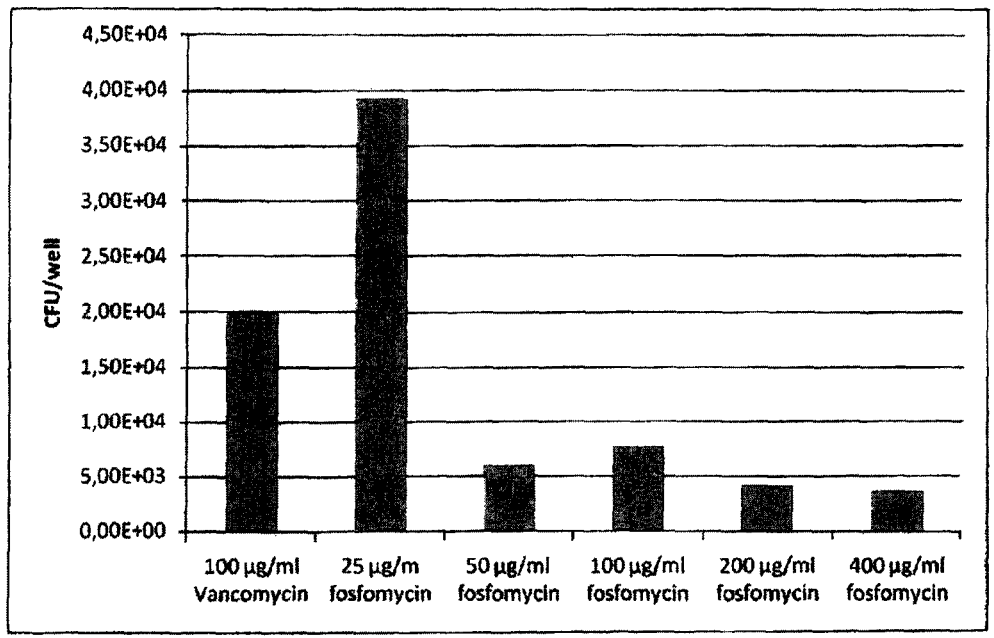
FIG. 4a shows CFU of *S.aureus* BAA44 located in osteoblastic MG63 cells after adding fosfomycin to the cell culture supernatant of osteoblastic MG63 cells after treatment with lysostaphin to remove extracellular bacteria.

Fosfomycin in concentration between 50-400 µg/ml shows a good efficacy on the infection rate with intracellular located S.aureus BAA44 (FIG. 4a). Surprisingly the effect of fosfomycin can be achieved at concentrations allowing for intravenous application (100-400 µg/ml, preferably 132-297 µg/ml in serum). Because of its excellent tissue penetration high fosfomycin concentrations are also achieved in bone. Therefore, fosfomycin is successfully applied in the treatment of osteomyelitis.

The person skilled in the art will recognize that the above given description is just one possibility out of many alternatives.

Figure 4B:
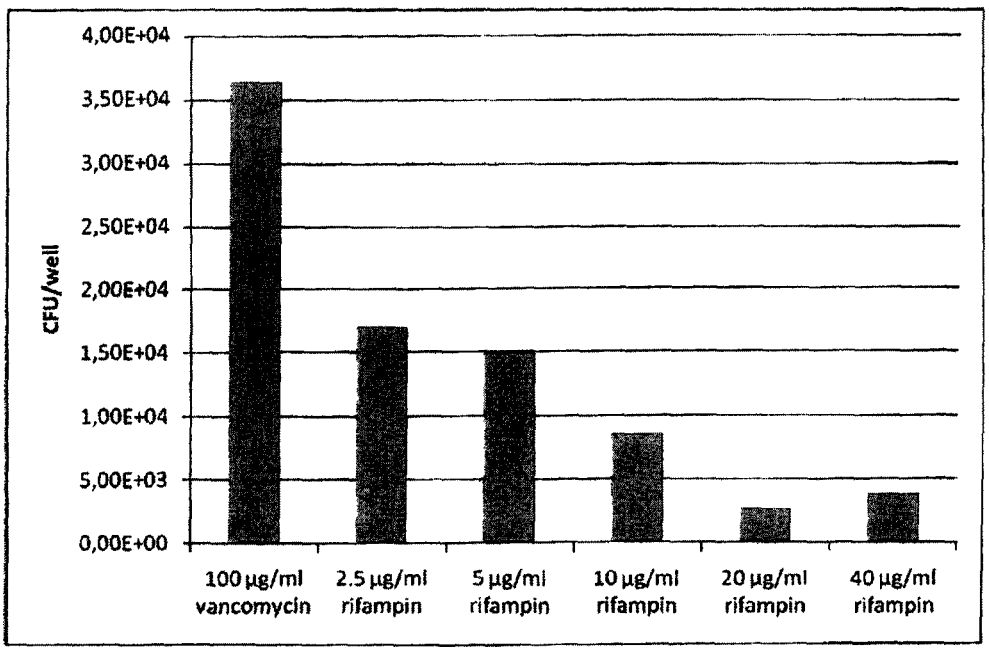
FIG. 4b shows CFU of *S.aureus* BAA44 located in osteoblastic MG63 cells after adding rifampin to the cell culture supernatant of osteoblastic MG63 cells after treatment with lysostaphin to remove extracellular bacteria.
Figure 4C:
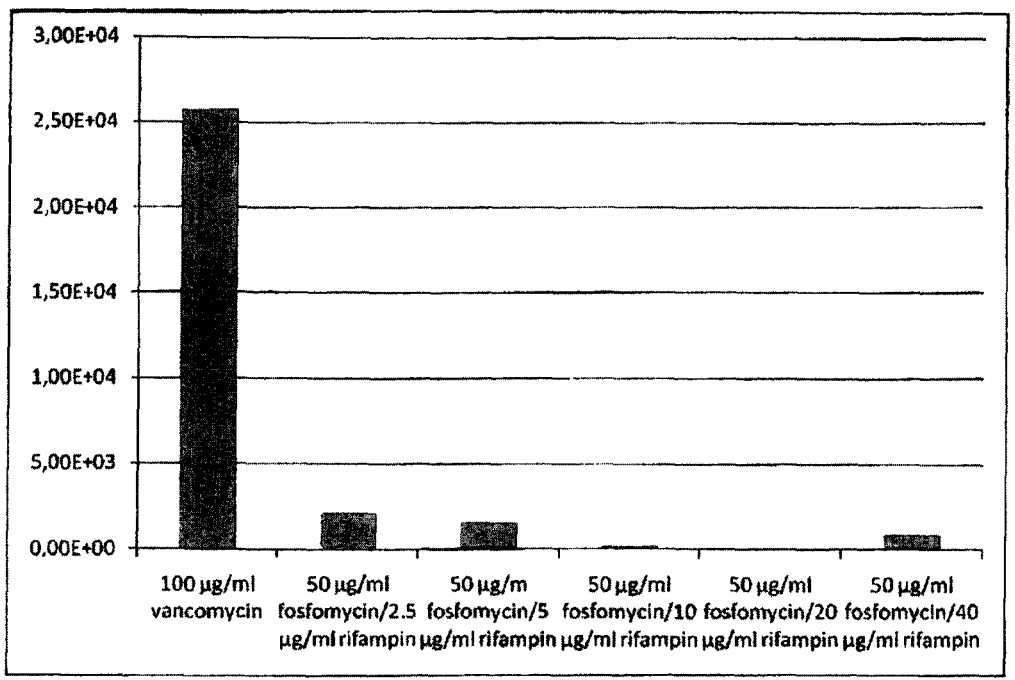
FIG. 4c shows CFU of *S.aureus* BAA44 located in osteoblastic MG63 cells after adding a mixture containing 50 µg/ml fosfomycin and 2.5-40 µg/ml rifampin to the cell culture supernatant of osteoblastic MG63 cells after treatment with lysostaphin to remove extracellular bacteria.
Figure 4D:
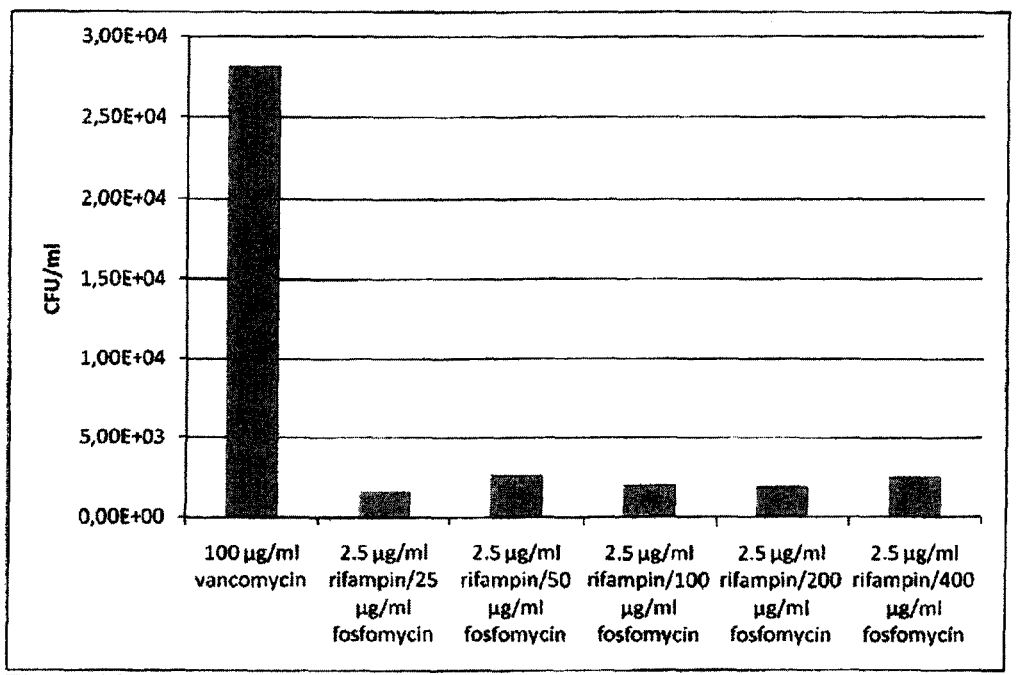
FIG. 4d: shows CFU of *S.aureus* BAA44 located in osteoblastic MG63 cells after adding a mixture containing 25-400 µg/ml fosfomycin and 2.5 µg/ml rifampin to the cell culture supernatant of osteoblastic MG63 cells after treatment with lysostaphin to remove extracellular bacteria.
Figure 4E:
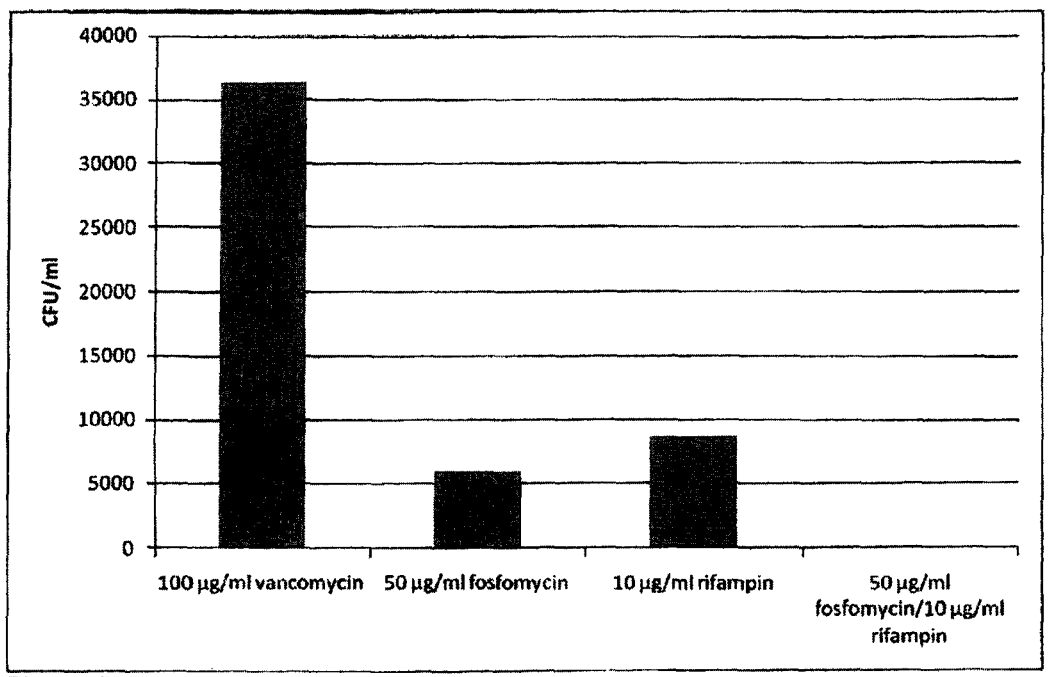
FIG. 4e shows CFU of *S.aureus* BAA44 located in osteoblastic MG63 cells after adding fosfomycin, rifampin and a mixture containing 50 µg/ml fosfomycin and 10 µg/ml rifampin to the cell culture supernatant of osteoblastic MG63 cells after treatment with lysostaphin to remove extracellular bacteria.
Figure 4F:
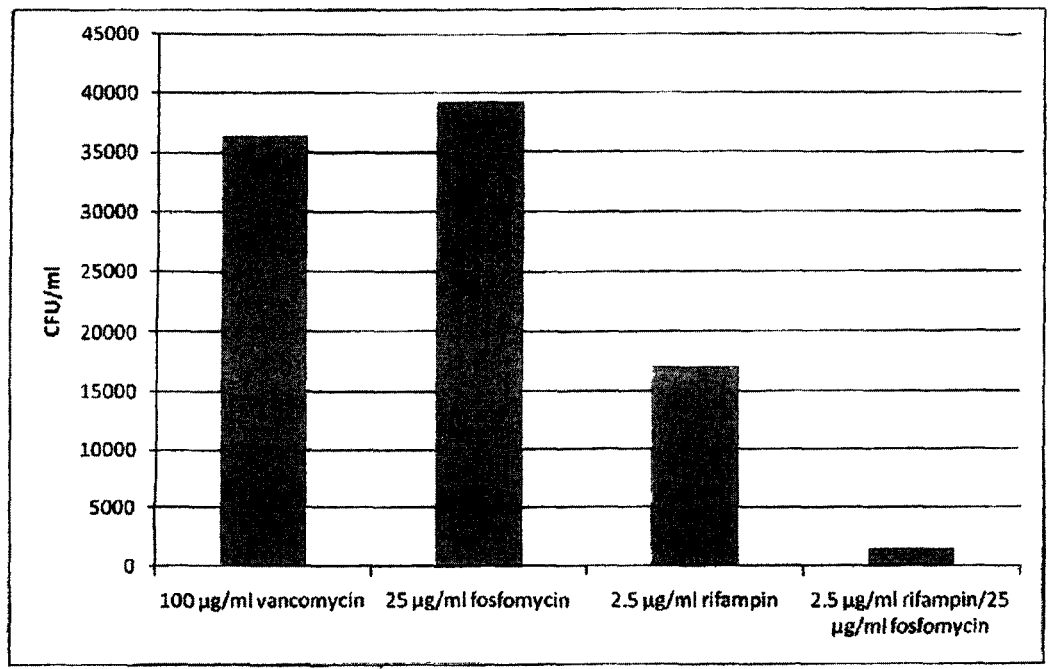
FIG. 4f shows CFU of *S.aureus* BAA44 located in osteoblastic MG63 cells after adding fosfomycin, rifampin and a mixture containing 25 µg/ml fosfomycin and 2.5 µg/ml rifampin to the cell culture supernatant of osteoblastic MG63 cells after treatment with lysostaphin to remove extracellular bacteria.
Figure 4G:
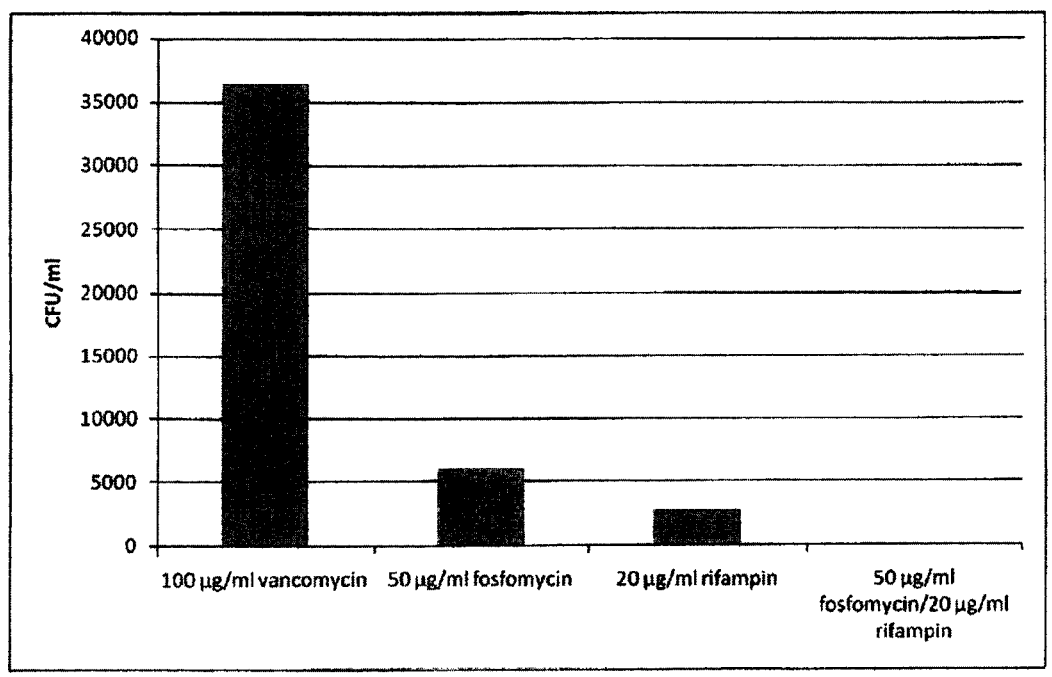
FIG. 4g: shows CFU of *S.aureus* BAA44 located in osteoblastic MG63 cells after adding fosfomycin, rifampin and a mixture containing 50 µg/ml fosfomycin and 20 µg/ml rifampin to the cell culture supernatant of osteoblastic MG63 cells after treatment with lysostaphin to remove extracellular bacteria.

Although S.aureus BAA44 is a rifampin resistant strain rifampin shows a good intracellular potency (FIG. 4b).

Rifampin and fosfomycin show clearly a synergistic effect in varying concentration ratios (FIG. 4c-g).

Even in case of the rifampin resistant S.aureus BAA44 the applied concentrations were sufficient enough in order to allow a systemic treatment of bone infections. Therefore, the combination of rifamycin and fosfomycin is suitable for treating osteomyelitis and can also be applied systemically.

3. Use of a Combination of Rifampin and Fosfomycin as Anti-Adhesives on Surfaces of Medical Substrates 3.1. Adhesion of *Staphylococcus aureus* subsp. *aureus* Rosenbach (ATTC 6538P) on a Titanium Substrate Coated with Rifampin and Fosfomycin An overnight culture of S.aureus ATTC 6538P was prepared by infecting 5 ml Caso-Bouillon medium with S.aureus ATTC 6538P. The cultures were incubated with shaking (450 U/min) over night at 37° C. 100 µl of the overnight cultures were transferred into 5 ml Caso Bouillon medium and incubated for 2 h at 37° C. with shaking (450 U/min). The bacterial density was determined photometrically. The bacterial suspension was diluted 1:2 in Caso Bouillon prior measurement. A bacterial suspension with a density of $1\times10^5$ CFU/ml in Caso Boullion with 10% FCS was used for the adhesion experiments.

Differently coated 2 cm titanium discs were used as samples:
- titanium discs sand blasted as negative control,
- titanium discs sand blasted and coated with 200 µg/cm² vancomycin,
- titanium discs simultaneously coated with 50 µg/cm² rifampin and 200 µg/cm² fosfomycin calcium,
- titanium discs coated in a first step with 50 µg/cm² rifampin and in a second step with 200 µg/cm² fosfomycin calcium, and
- titanium discs coated in a first step with 200 µg/cm² fosfomycin calcium and in a second step with 50 µg/cm² rifampin.

After coating the titanium discs were washed either one time or three times with PBS. The coated and uncoated titanium discs were incubated for 5 min at room temperature with 5 ml PBS. This was repeated two more times. In the third circle the titanium discs were incubated for 1 h at room temperature. Before removing the PBS solution the titanium discs were turned or swiveled in order to increase the detachment of the antibiotics. Afterwards the titanium discs were transferred into sterile 12 well plates.

The different titanium samples were incubated with 2 ml bacterial suspension for 1.5 h at 37° C. without shaking.

Afterwards the bacterial suspension was removed and the discs were washed three times with 2.5 ml PBS. After the last washing cycle each discs was placed in 10 ml sterile ringer's solution. Only one disc of each group was simultaneously examined while the other discs were stored at 4° C. The titanium discs in the ringer's solution were exposed to ultra sound for 10 min in order to detach the adhered bacteria. The suspensions comprising the detached bacteria were diluted (1:10, 1:100) and streaked out on a Caso agar plate. The agar plates were incubated over night at 37° C. and the next day the colonies were counted.

The person skilled in the art will recognize that the above given description is just one possibility out of many alternatives.

Figure 5A:
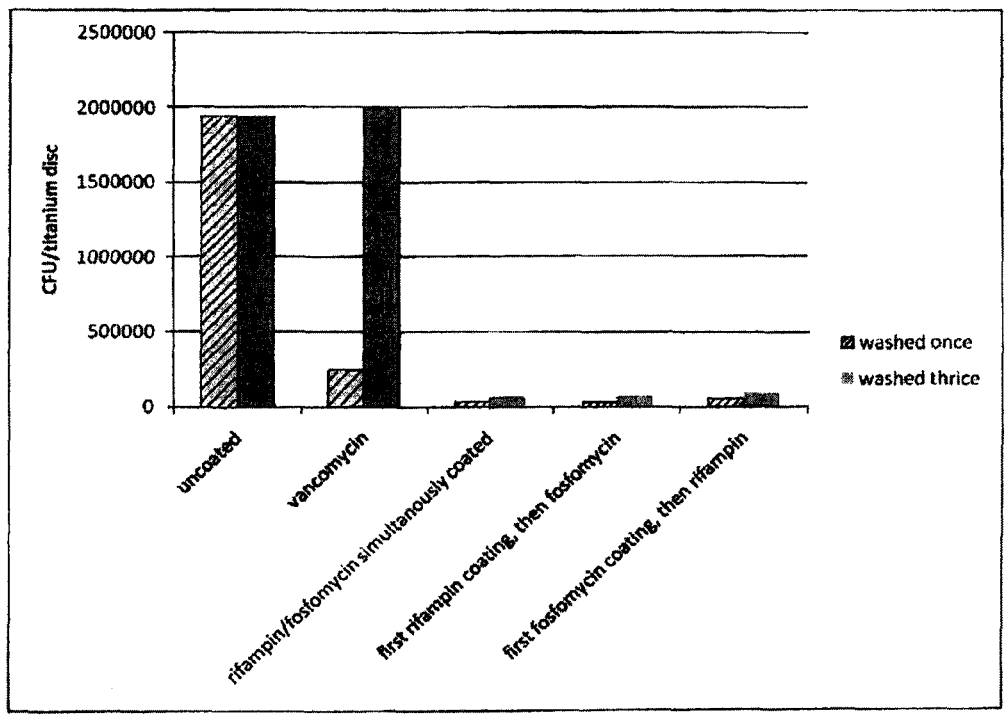
FIG. 5a: shows CFU of *S.aureus* ATTC 6538P per titanium disc after 1.5 h incubation of *S.aureus* on vancomycin or rifampin/fosfomycin coated titanium disc, which were either washed once or thrice before incubation.

FIG. 5a shows the CFU of S.aureus ATTC 6538P per titanium disc after incubation for 1.5 h with the bacteria. Vancomycin had only an anti-adhesive effect after one washing step, but did not reveal any anti-adhesive effect after three washing steps. In fact, the number of S.aureus cells adhered to the vancomycin coated discs was identical to the uncoated discs. However, the combination rifampin and fosfomycin showed a strong anti-adhesive effect. The effect depended only slightly on the number of washing steps. Obviously, the rifampin/fosfomycin coating was less likely to be removed completely from the titanium surface by several washing steps than vancomycin.

The order of coating the discs with rifampin and fosfomycin—together, first rifampin then fosfomycin; first fosfomycin then rifampin—does not seem to influence the effect (FIG. 5a).

3.2. Adhesion of *Staphylococcus epidermis* ATTC 35984 on a Titanium Substrate Coated with a Combination of Rifampin and Fosfomycin The experimental set up was essentially the same as described above for S.aureus ATTC 6538P.

Differently coated 2 cm titanium discs were used as samples:
- titanium discs (sand blasted) as negative control,
- titanium discs coated in a first step with 50 µg/cm² rifampin and in a second step with 200 µg/cm² fosfomycin calcium, and
- titanium discs coated in a first step with 200 µg/cm² fosfomycin calcium and in a second step with 50 µg/cm² rifampin.

The coated titanium discs were washed three times with 5 ml PBS before incubation with S.epidermis.

The person skilled in the art will recognize that the above given description is just one possibility out of many alternatives.

Figure 5B:
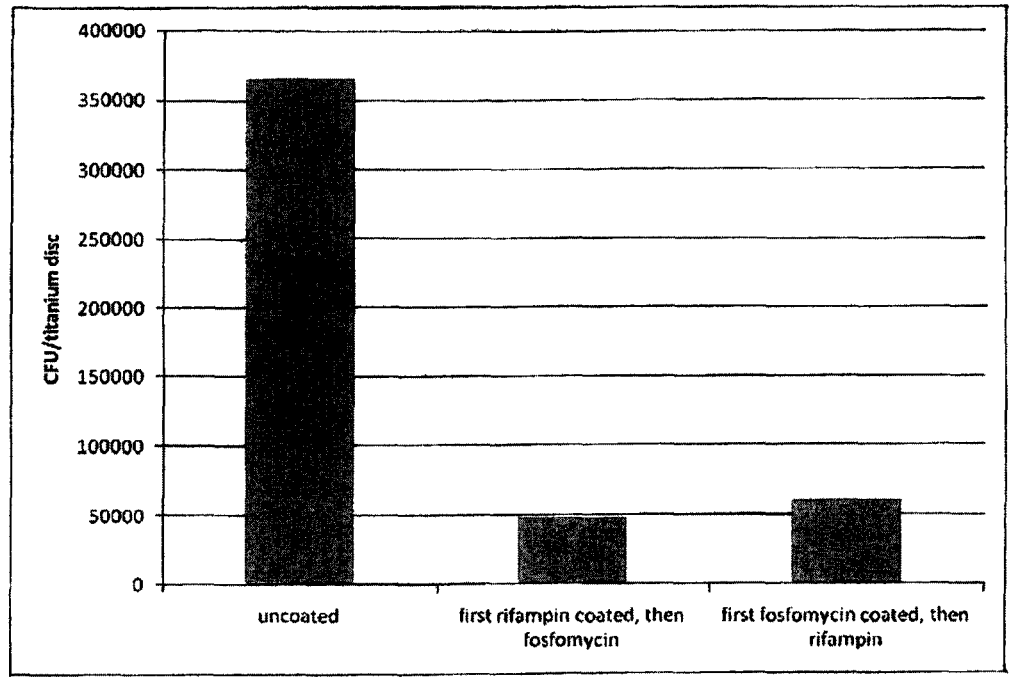
FIG. 5b: shows CFU of *S.epidermidis* ATTC 35984 per titanium disc after 2 h incubation with *S.epidermis* on rifampin/fosfomycin coated titanium discs, which were washed twice before incubation.

The experimental results for S.epidermis (FIG. 5b) support the results found in case of S.aureus ATTC6538P. The adhesion of S.epidermis ATTC 35984 on uncoated titanium was lower than the adhesion of S.aureus ATTC6538P. This can relate to the fact that S.epidermis preferably attaches to plastics or hydroxyapatite but less to titanium. Although the titanium discs were washed three times before incubation with the bacteria, the combination rifampin and fosfomycin shows a strong anti-adhesive effect.

3.3. Adhesion of *Staphylococcus aureus* BAA44 on a Titanium Substrate Coated with a Combination of Rifampin and Fosfomycin The experimental set up was essentially the same as described above for S.aureus ATTC 6538P.

The following coated 2 cm titanium discs were used as samples:
- titanium discs sand blasted as negative control,
- titanium discs coated with 200 µg/cm² vancomycin
- titanium discs sand blasted and coated in a first step with 50 µg/cm² rifampin and in a second step with 200 µg/cm² fosfomycin calcium.

The coated titanium discs were washed either once or twice with 5 ml PBS before incubation with S.aureus BAA44 for 1.5 h.

The person skilled in the art will recognize that the above given description is just one possibility out of many alternatives.

Figure 5C:
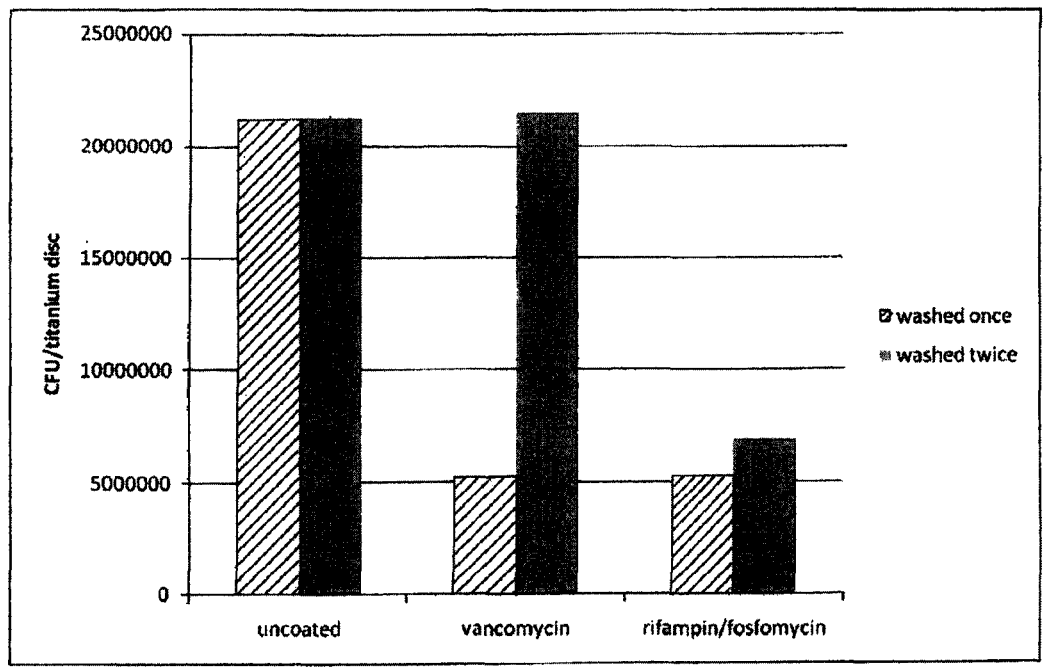
FIG. 5c: shows CFU of *S.aureus* BAA44 per titanium disc after 1.5 h incubation of with *S.aureus* on vancomycin or rifampin/fosfomycin coated titanium discs, which were washed either once or twice before incubation.

FIG. 5c shows the CFU on the discs after incubation with S.aureus BAA44. Vancomycin reduced the adhesion of S.aureus BAA44 only if the disc were washed once: After two washing steps all vancomycin seems to be removed and no reduction of bacterial adhesion could be observed. Despite the rifampin-resistance of S.aureus BAA44 the combination rifampin/fosfomycin had a strong anti-adhesive effect, which was only slightly diminished if the discs were washed twice instead of once before incubation with the bacteria.

3.4. Bactericidal Activity of Titanium Substrate Coated with Rifampin and Fosfomycin against S.aureus BAA44

An overnight culture of S.aureus BAA44 was prepared by infecting 5 ml Caso-Bouillon medium with S.aureus BAA44. The cultures were incubated with shaking (450 U/min) over night at 37° C. 100 µl of the overnight cultures were transferred into 5 ml Caso Bouillon medium and incubated for 2 h at 37° C. with shaking (450 U/min) prior to the incubation with the titanium discs. The bacterial density was determined photometrically.

A bacterial suspension with a density of $1\times10^4$ CFU/ml in Minimal Medium (PBS, 0.2% ammonium chloride, 0.2% sodium sulphate, 0.25% glucose, 1% Caso Bouillon, 50 µg/ml glucose-6-phosphate) was used in the adhesion assay. The Minimal Medium was used instead of Caso Bouillon to minimize the bacterial growth.

Differently coated 2 cm titanium discs were used as samples:
  titanium discs (sand blasted) as negative control,
  titanium discs (sand blasted) coated with 200 µg/cm² vancomycin,
  titanium discs coated in a first step with 300 µg/cm² fosfomycin calcium and in a second step with 70 µg/cm² rifampin.

After coating, the titanium discs were washed three times with 2.5 ml PBS at room temperature.

The different titanium samples were incubated with 2 ml bacterial suspension for 15.5 h at 37° C. without shaking.

Afterwards the CFU in the supernatant as well as the adhered bacteria on the titanium discs were analysed. The supernatant was diluted 1:10 in PBS, 100 µl of the dilution were streaked out on Caso agar plates. The discs were washed four times with 2.5 ml PBS to remove not adherent bacteria. After the last washing cycle each discs was placed in 10 ml sterile ringer's solution. Only one disc of each group was simultaneously examined while the other discs were stored at 4° C. The titanium discs in the ringer's solution were exposed to ultra sound for 10 min in order to detach the adhered bacteria. The suspensions comprising the detached bacteria were diluted (1:10, 1:100, 1:1000) and streaked out on a Caso agar plate. The agar plates were incubated over night at 37° C. and the next day the colonies were counted.

The person skilled in the art will recognize that the above given description is just one possibility out of many alternatives.

Figure 5D:
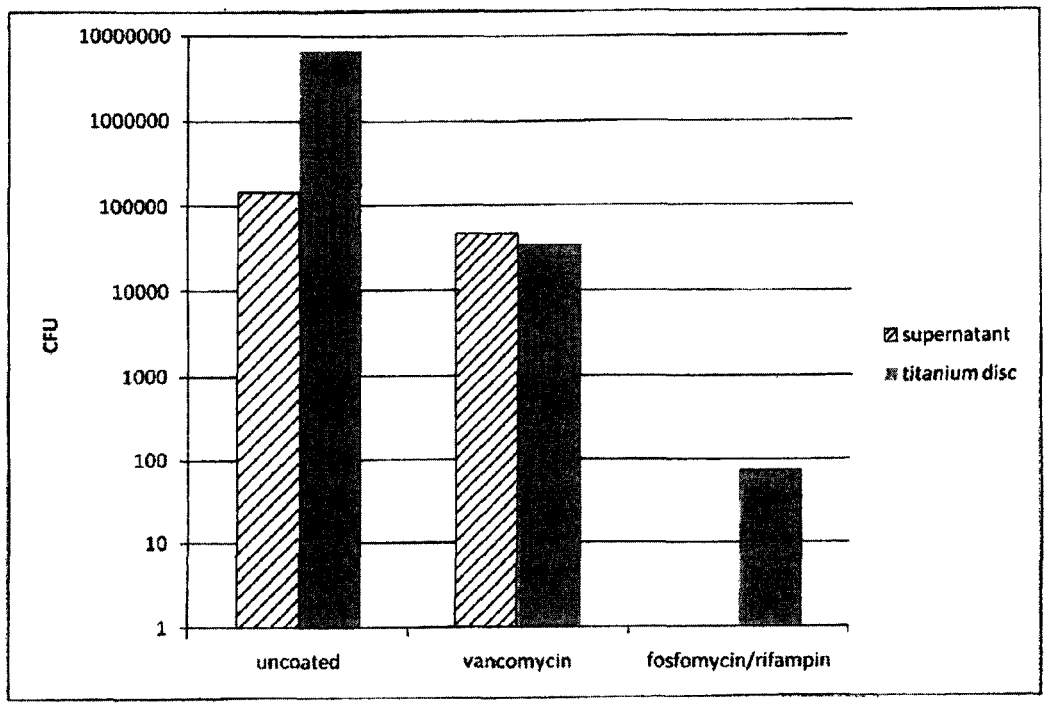
FIG. 5d: shows CFU of *S.aureus* BAA44 on titanium discs or in the supernatant after overnight incubation of *S.aureus* with vancomycin or rifampin/fosfomycin coated titanium discs in Minimal Medium.

The results are shown in FIG. 5d. The bacterial growth in the negative controls was reduced by using Minimal Medium, but nevertheless the bacterial CFU in the supernatant increased ten times during the incubation period. Surprisingly, more CFU could be found adhered to the uncoated disc than in the supernatant.

Vancomycin reduced the bacterial growth in the cell culture supernatant compared to the uncoated control slightly, but the adherence of the bacteria was even more reduced. However, vancomycin could not exhibit any bactericidal effect and more than 50,000 CFU could be found on the vancomycin coated titanium samples.

Although the titanium discs were washed three times before the adhesion assay, the fosfomycin/rifampin combination displayed a clear bactericidal activity against the rifampin-resistant strain BAA44. No CFU could be detected in the supernatant and less than 100 CFU adhered to the titanium surface. This corresponds to a 86,000-fold reduction in bacterial adherence compared to uncoated titanium and a 470-fold reduction compared to the vancomycin coating.

It was expected that a soluble antibiotic coating without carrier matrix e.g. polymer matrix unfolds its efficacy by dissolving into the tissue fluid after implantation. The colonization of the implant or prosthesis is then hampered by killing the planktonic bacteria before colonization and reduction of bacterial propagation due to the efficacy of the dissolved antibiotics. After several washing steps the amount of rifampin and fosfomycin left on the discs, and thus available in the supernatant, was still high enough for showing antibacterial efficacy in the supernatant. Therefore, the rifampin/fosfomycin coating is stable enough to get in contact with tissue fluids and blood during implantation and is still effective in preventing bacterial adherence to the implant surface and the surrounding tissue. This property is especially important for staphylococci infections, because staphylococci do not adhere exclusively to implants but to the extracellular matrix of tissue as well.

4. Use of Rifampin and Daptomycin or their Combination for Treatment of Acute Infection of Osteoblasts MG63 cells with *Staphylococcus aureus* subsp. *aureus* (BAA44)

Osteoblastic MG63 cells were detached with the cell detachment medium Accutase 24 hours before infection. The cell number was determined using the Neubauer counting chamber. Cells were seeded onto uncoated 24 well plates with a cell density of $1.5 \times 10^4$ cells/cm² in 1 ml DMEM (Dulbecco's Modified Eagle's Medium) with 10% FCS (fetal calf serum), 1% Glutamax-I and 1% Natrium Pyruvat and incubated at 37° C. and 5% $CO_2$.

An overnight culture of *S.aureus* BAA44 was prepared by infecting 5 ml Caso-Bouillon medium with *S.aureus* BAA44. The cultures were incubated with shaking (450 U/min) over night at 37° C. 100 µl of the overnight cultures were transferred into 5 ml Caso Bouillon medium and incubated for 2 h at 37° C. with shaking (450 U/min) prior to infection.

The cell culture supernatant of the osteoblastic MG63 cells was removed with a pipette from the wells. 1 ml containing $1 \times 10^6$ *S.aureus* BAA44 CFU was added to each well containing also antibiotics having the following compositions:
  50 µg/ml vancomycin
  2.5 µg/ml rifampin
  1.25-10 µg/ml daptomycin
  and their mixtures in different ratios as given below.

The combined osteoblastic cells, bacteria, and antibiotic compositions were incubated for 18 h at 37° C. under 5% $CO_2$ atmosphere.

Afterwards the cells were washed once with PBS pH 7.4 (phosphate buffer solution) followed by lysis with 1 ml 0.1% Triton X100 in ringer's solution. The lysates were thoroughly resuspended with a pipette. Only one 24 well plate was handled and the other plates were stored at 4° C. in order to minimize bacterial growth in the lysate. The lysates were diluted 1:10 in PBS, 100 µl of diluted lysate were streaked out on Caso agar plates, incubated over night at 37° C. and the colonies were counted.

The person skilled in the art will recognize that the above given description is just one possibility out of many alternatives.

Figure 6:
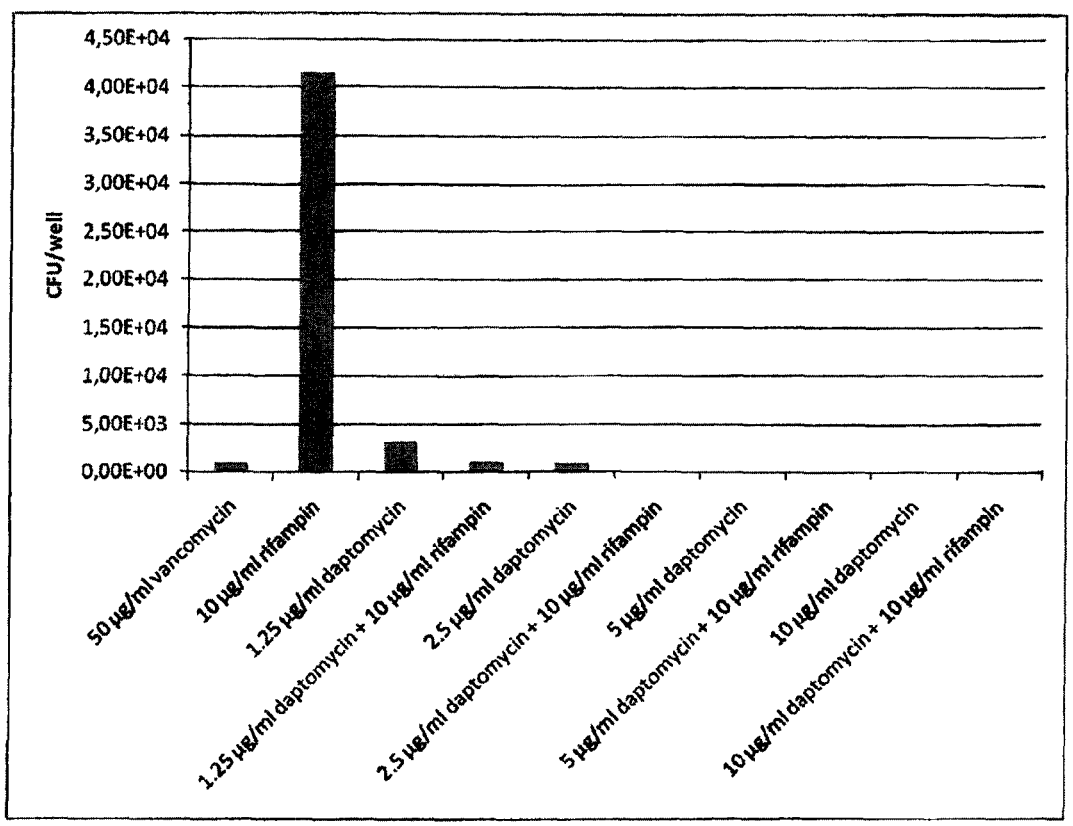
FIG. 6: shows CFU of in osteoblastic MG63 cells intracellular located or to osteoblastic MG63 cells adhered *S.aureus* BAA44 after incubation overnight with *S.aureus* BAA44 and antibiotics.

Because the cells were not treated with lysostaphin after infection, the CFU value per well (FIG. 6) is an indicator for the degree of intracellular infection of osteoblastic MG63 cells with *S.aureus* BAA44 as well as for *S.aureus* BAA44 adhered extracellularly to osteoblastic MG63 cells. The lower the CFU value is the lower is the infection rate of the osteoblastic cells with *S.aureus* BAA44. This correlates to the efficacy of the added antibiotic.

Because the strain is rifampin-resistant the effect of 2.5 µg rifampin was less than for vancomycin and daptomycin, but overgrowth of the MG63 cells with planktonic *S.aureus* BAA44 was prevented efficacious (data not shown)

Daptomycin alone showed good efficacy already in concentrations of 1.25 µg/ml and 2.5 µg/ml, whereas 5 µg/ml and 10 µg/ml could eradicate the infection completely.

Despite the ineffectiveness of rifampin alone, the combination 2.5 µg/ml rifampin and 1.25 µg/ml or 2.5 µg/ml daptomycin respectively was synergistic in eliminating all intracellular and extracellular adhered bacteria.

Because vancomycin is only weak bactericidal a very high concentration of vancomycin was used in this experiment to increase its efficacy. This concentration can never be achieved by intravenous application of vancomycin. However, several hundred *S. aureus* could escape vancoymicin by invading the osteoblastic cells, a phenomenon that has relevance in vivo especially in the treatment of bone infections.

Daptomycin is in contrast to glycopeptides like vancomycin rapidly bactericidal and the bactericidal activity is concentration dependent. Therefore the higher concentrations of 5 and 10 µg/ml could eliminate all bacteria before they were able to invade the osteoblastic cells.

Local application of rifampin and daptomycin could be an efficient treatment for acute bone infections. Daptomycin eliminates in high concentrations very efficiently all extracellular bacteria and thus prevents infection of new osteoblasts, while rifampin is able to eradicate intracellular infected osteoblasts.

5. Coated or Impregnated Substrates for Medical Purposes

Rifampin was diluted in methanol in a concentration of 30-40 mg/ml. Fosfomycin calcium was suspended in ultrapure water in a concentration of 100-140 µg/ml. No further additives were used. The titanium endoprosthesis with different surface modifications (sand-blasted, porous coated, or hydroxyapatite coated) was coated directly with the antibiotic solutions using the ink-jet or the spray coating process. The surface can be coated with rifampin first, followed by fosfomycin calcium, the other way around, or both antibiotics simultaneously. The resulting covering density was 50-70 µg/cm² rifampin and 300-350 µg/cm² fosfomycin.

Rifampin, fosfomycin disodium, and fosfomycin calcium were incorporated into collagen fleeces during the production process of the fleeces. Rifampin and fosfomycin disodium were added dissolved in acidified buffer, while fosfomycin calcium was added in watery suspension. The final concentrations were 0.1-0.2 mg rifampin per cm² collagen fleece and 0.5 mg-2 mg fosfomycin per cm² collagen fleece, whereas fosfomycin disodium and fosfomycin calcium could contribute in varying proportions to the final concentration of fosfomycin.

Rifampin and fosfomycin disodium were mixed with two different polymers on PMMA basis, zirconium dioxide, and glycine. Rifampin was added in an amount of 0.5-1.5% of the total weight, while fosfomycin disodium was added in an amount of 2.5-7.5% of the total weight. The polymer/antibiotic mixture was heated to 160-180° C. and PMMA beads were manufactured directly on metal wires by injection moulding.

The person skilled in the art will recognize that the above given description is just one possibility out of many alternatives.

Numerous modifications and variations of practicing the present invention are possible in light of the above teachings and therefore will fall within the scope of the following claims.

The invention claimed is:

1. A pharmaceutical composition formulated for the local prevention or local treatment of tissue infection associated with gram-positive bacteria at a site of implantation of a prosthesis, occurring due to a surgical operation related to the implantation of the prosthesis, wherein the pharmaceutical composition consists of (i) 0.005 to 100 µg/ml rifampin and 1 to 1000 µg/ml fosfomycin or (ii) 0.005 to 100 µg/ml rifampin and 0.1 to 100 µg/ml daptomycin.

2. The pharmaceutical composition according to claim 1, consisting of rifampin and fosfomycin.

3. The pharmaceutical composition according to claim 1, consisting of rifampin and daptomycin.

4. A pharmaceutical composition for the prevention of microbial infection in cells, or for the treatment of extracellular microbial infected cells, intracellular microbial infected cells, or a combination thereof, the composition consisting of (i) 0.005 to 100 µg/ml rifampin and 1 to 1000 µg/ml fosfomycin, or (ii) 0.005 to 100 µg/ml rifampin and 0.1 to 100 µg/ml daptomycin, formulated for local administration to a site of an orthopedic procedure.

5. A pharmaceutical composition according to claim 4, wherein the composition is formulated for localized injection to a subject.

6. A pharmaceutical composition according to claim 4, wherein the cells are osteoblasts, leucocytes, erythrocytes, keratinocytes, fibroblasts, fat cells, muscle cells, endothelial cells, or a combination thereof.

7. A pharmaceutical composition according claim 4, wherein the microbial infection is caused by gram-positive bacteria.

8. A substrate configured to be a carrier for local antimicrobial antibiotic therapy, comprising a pharmaceutical composition according to claim 1.

9. A substrate according to claim 8, wherein the pharmaceutical composition constitutes 0.5% to 7.5% of the total weight of the substrate.

10. A substrate according to claim 8, wherein the substrate comprises a fleece, a fabric, a polymethyl methacrylate, a copolymer of methylmethacrylate and methylacrylate, a biodegradable polymer, polyethylene, a metal, a metal alloy, a ceramic, a bone cement, a bone substitute, a polylactide, a calcium phosphate, collagen, or a combination thereof.

11. A substrate according to claim 8, wherein the pharmaceutical composition has a density of 10 to 10,000 µg/cm² of the substrate surface area.

12. A substrate according to claim 8, wherein the substrate comprises an implantable prosthesis.

13. An implant coated with a pharmaceutical composition according to claim 1.

14. The composition according to claim 1, wherein the composition consists of rifampin and fosfomycin, the rifampin being in an amount sufficient to provide a concentration of 0.006 to 80 µg/ml rifampin at the site to be treated, and the fosfomycin being in an amount sufficient to provide a concentration of 5 to 800 µg/ml fosfomycin at the site to be treated.

15. The composition according to claim 1, wherein the composition consists of rifampin and fosfomycin, the rifampin being in an amount sufficient to provide a concentration of 0.0075 to 10 µg/ml rifampin at the site to be treated, and the fosfomycin being in an amount sufficient to provide a concentration of 10 to 200 µg/ml fosfomycin at the site to be treated.

16. The composition according to claim 1, wherein the composition consists of rifampin and daptomycin, the rifampin being in an amount sufficient to provide a concentration of 0.006 to 80 µg/ml rifampin at the site to be treated, and the daptomycin being in an amount sufficient to provide a concentration of 0.5 to 80 µg/ml daptomycin at the site to be treated.

17. The composition according to claim 1, wherein the composition consists of rifampin and daptomycin, the rifampin being in an amount sufficient to provide a concentration of 0.0075 to 20 µg/ml rifampin at the site to be treated, and the daptomycin being in an amount sufficient to provide a concentration of 1 to 20 µg/ml daptomycin at the site to be treated.

* * * * *

UNITED STATES PATENT AND TRADEMARK OFFICE
CERTIFICATE OF CORRECTION

PATENT NO. : 9,968,710 B2
APPLICATION NO. : 14/566465
DATED : May 15, 2018
INVENTOR(S) : Nicole Duewelhenke Page 1 of 1

It is certified that error appears in the above-identified patent and that said Letters Patent is hereby corrected as shown below:

On the Title Page

On page 2, in Column 2, under "Other Publications", Line 11, delete "Cariovascular" and insert --Cardiovascular-- therefor On page 2, in Column 2, under "Other Publications", Line 22, delete "Venouse" and insert --Venous-- therefor On page 3, in Column 1, under "Other Publications", Line 36, delete "reciew"," and insert --review",-- therefor On page 3, in Column 1, under "Other Publications", Line 54, delete "skeetal" and insert --skeletal-- therefor In the Claims In Column 20, Line 16, in Claim 7, after "according", insert --to--

Signed and Sealed this
Second Day of April, 2019

Andrei Iancu
*Director of the United States Patent and Trademark Office*